(12) United States Patent
Nakatani et al.

(10) Patent No.: US 8,232,084 B2
(45) Date of Patent: Jul. 31, 2012

(54) DEVICE FOR MEASURING EXTRACELLULAR POTENTIAL AND METHOD OF MANUFACTURING DEVICE

(75) Inventors: Masaya Nakatani, Hyogo (JP); Hiroaki Oka, Osaka (JP); Fumiaki Emoto, Osaka (JP)

(73) Assignee: Panasonic Corporation, Osaka (JP)

( * ) Notice: Subject to any disclaimer, the term of this patent is extended or adjusted under 35 U.S.C. 154(b) by 374 days.

(21) Appl. No.: 12/245,091

(22) Filed: Oct. 3, 2008

(65) Prior Publication Data

US 2009/0035846 A1    Feb. 5, 2009

Related U.S. Application Data

(63) Continuation of application No. 10/485,644, filed as application No. PCT/JP03/06920 on Jun. 2, 2003, now Pat. No. 7,501,278.

(30) Foreign Application Priority Data

Jun. 5, 2002 (JP) ................................. 2002-163934
Aug. 1, 2002 (JP) ................................. 2002-224563

(51) Int. Cl.
*C12N 13/00* (2006.01)
*C12M 1/42* (2006.01)
*C12M 3/00* (2006.01)

(52) U.S. Cl. ............... 435/173.4; 435/288.4; 435/173.7; 435/285.2; 435/288.3; 435/305.2; 435/173.5; 435/288.2; 435/30; 435/305.3; 435/173.6; 204/403.01

(58) Field of Classification Search ............... 435/173.4, 435/288.4, 173.7, 285.2, 288.3, 305.2, 173.5, 435/288.2, 30, 305.3, 173.6; 204/403.01
See application file for complete search history.

(56) References Cited

U.S. PATENT DOCUMENTS 5,183,744 A    2/1993    Kawamura et al.
(Continued)

FOREIGN PATENT DOCUMENTS

EP         0 652 308 B1    5/1995
(Continued)

OTHER PUBLICATIONS

International Search Report issued Aug. 26, 2003 in the International (PCT) Application of which the present application is the U.S. National Stage.

(Continued)

*Primary Examiner* — Nathan Bowers
(74) *Attorney, Agent, or Firm* — Wenderoth, Lind & Ponack, L.L.P.

(57) ABSTRACT

A device for measuring an extracellular potential of a test cell includes a substrate having a well formed in a first surface thereof and a first trap hole formed therein. The well has a bottom. The first trap hole includes a first opening formed in the bottom of the well and extending toward a second face of the substrate, a first hollow section communicating with the first opening via a first connecting portion, and a second opening extending reaching the second surface and communicating with the first hollow section via a second connecting portion. The first connecting portion has a diameter smaller than a maximum diameter of the first hollow section, greater than a diameter of the second connecting portion, and smaller than a diameter of the test cell. The device can retain the test cell securely and accept chemicals and the test cell to be put into the device easily.

11 Claims, 20 Drawing Sheets

U.S. PATENT DOCUMENTS

| | | |
|---|---|---|
| 6,413,792 B1 | 7/2002 | Sauer et al. |
| 6,682,649 B1 | 1/2004 | Petersen et al. |
| 6,776,896 B1 | 8/2004 | Osipchuk |
| 6,984,297 B2 | 1/2006 | Nisch et al. |
| 7,006,929 B2 | 2/2006 | Oka et al. |
| 7,501,278 B2 | 3/2009 | Nakatani et al. |
| 2002/0182627 A1 | 12/2002 | Wang et al. |
| 2003/0113833 A1 | 6/2003 | Oka et al. |
| 2004/0033483 A1 | 2/2004 | Oka et al. |
| 2005/0221469 A1 | 10/2005 | Nakatani et al. |
| 2006/0228771 A1* | 10/2006 | Dodgson et al. ............ 435/30 |

FOREIGN PATENT DOCUMENTS

| | | |
|---|---|---|
| JP | 2-131569 | 5/1990 |
| JP | 06-244257 | 9/1994 |
| JP | 9-211010 | 8/1997 |
| JP | 9-289886 | 11/1997 |
| JP | 2003-511668 | 3/2003 |
| JP | 2003-511699 | 3/2003 |
| JP | 2004-12215 | 1/2004 |
| JP | 2004-69309 | 3/2004 |
| JP | 2004-271330 | 9/2004 |
| JP | 2004-271331 | 9/2004 |
| WO | 99/66329 | 12/1999 |
| WO | 01/25769 | 4/2001 |
| WO | 01/27614 | 4/2001 |
| WO | 01/48474 | 7/2001 |
| WO | 02/055653 | 7/2002 |
| WO | 02/099408 | 12/2002 |
| WO | 03/016555 | 2/2003 |
| WO | 03/093494 | 11/2003 |

OTHER PUBLICATIONS

M. Watanabe et al., "Trial Micro-Channel Array for Cell Activity Analysis", Dai 6 kai Chino Mechatronics Workshop—Ningen o Shien suru Mechatronics Gijutsu-Koen Ronbunshu, Aug. 30, 2001, pp. 247-261 (with English translation).

European Search Report issued Jun. 7, 2010 in European Application No. EP 03 73 0758, which is a foreign counterpart of the present application.

European Search Report issued Jul. 8, 2011 in counterpart European Application No. 11 15 3679.3.

C. Schmidt, et al., "A Chip-Based Biosensor for the Functional Analysis of Single Ion Channels", Angewandte Chemie. International Edition, WileyVCH Verlag, vol. 39, No. 3137, Jan. 1, 2000, pp. 3137-3140.

* cited by examiner

DEVICE FOR MEASURING EXTRACELLULAR POTENTIAL AND METHOD OF MANUFACTURING DEVICE

This is a continuation application of U.S. application Ser. No. 10/485,644, filed Feb. 3, 2004 now U.S. Pat. No. 7,501,278, which is the National Stage of International Application No. PCT/JP03/06920, filed Jun. 2, 2003.

TECHNICAL FIELD

The present invention relates to a device for evaluating a biosample, such as a cell, easily and fast by measuring an extracellular potential an electrochemical change generated by the biosample. The present invention also relates to a method of manufacturing the device.

BACKGROUND ART

Drugs are generally screened according to electrical activities of the cell as an index by a patch clamp method or a method using a chemical, such as a fluorochrome or luminescence indicator. In the patch clamp method, a micro-electrode probe electrically records an ion transportation through a single channel of a protein molecule at a micro-section called "patch" of cell membrane attached to a tip of a micropipet. This method is one of the few methods that can evaluate functions of a protein molecule in real time. (Refer to "Molecular Biology of the Cell" third edition by Garland Publishing Inc. New York. 1994, written by Bruce Alberts et al. Japanese Edition "Molecular Biology of the Cell" pages 181-182, published from Kyouikusha Inc. 1995)

A fluorochrome or luminescence indicator which emits light in response to a change of a density of a specific ion monitors migration of the ion in a cell, thereby measuring the electrical activities of the cell.

The patch clamp method requires expertise for producing and operating the micropipet, and requires a long time to measure one sample, thus not being suitable for screening a large number of chemical-compound candidates. The method using the fluorochrome or the like can screen a large number of chemical-compounds candidates fast, but requires dyeing cells. A background of the cells may be colored due to pigment in measuring, and is decolorized according to a lapse of time, thus reducing an S/N ratio.

SUMMARY OF THE INVENTION

A device for measuring an extracellular potential of a test cell includes a substrate having a well formed in a first surface thereof and a first trap hole formed therein. The well has a bottom. The first trap hole includes a first opening formed in the bottom of the well and extending toward a second face of the substrate, a first hollow section communicating with the first opening via a first connecting portion, and a second opening extending reaching the second surface and communicating with the first hollow section via a second connecting portion. The first connecting portion has a diameter smaller than a maximum diameter of the first hollow section, greater than a diameter of the second connecting portion, and smaller than a diameter of the test cell.

The device can retain the test cell securely and accept chemicals and the test cell to be put into the device easily.

DESCRIPTION OF THE PREFERRED EMBODIMENTS

Exemplary Embodiment 1

Figure 1:
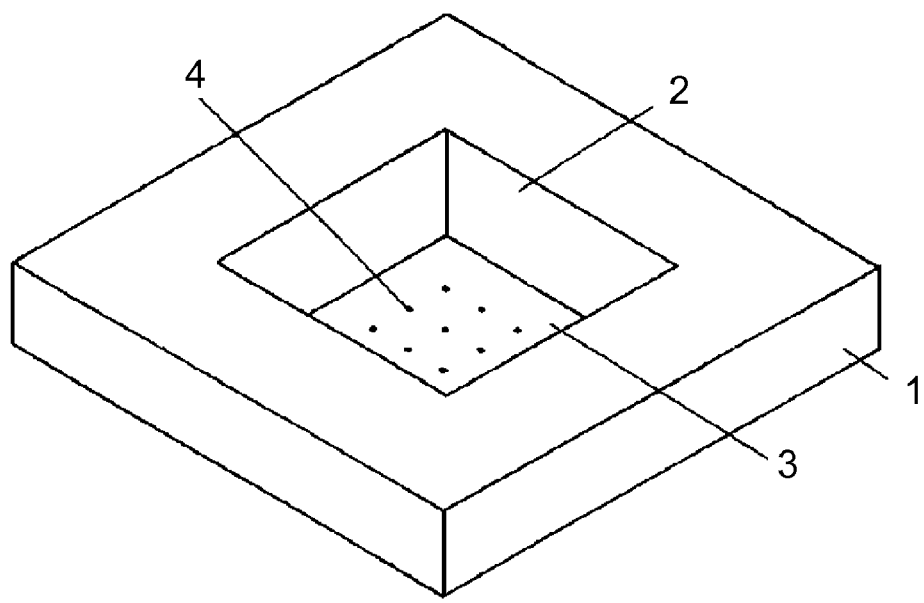
FIG. 1 is a perspective view of a device for measuring an extracellular potential in accordance with Exemplary Embodiment 1 of the present invention.
Figure 2:
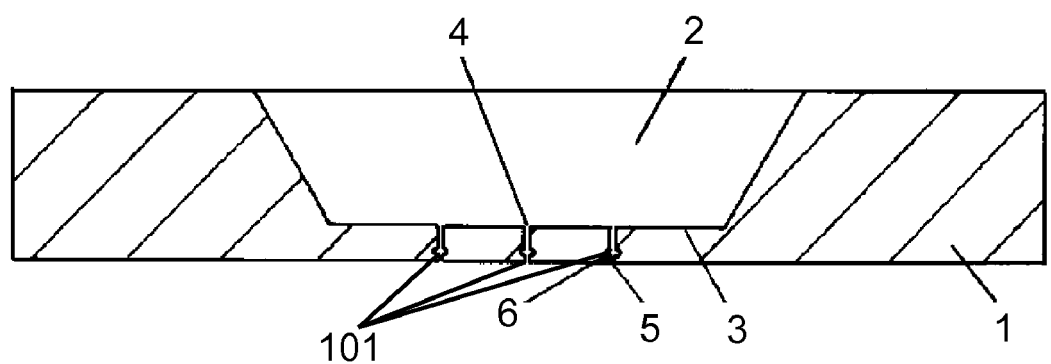
FIG. 2 is a sectional view of the device in accordance with Embodiment 1.
Figure 3:
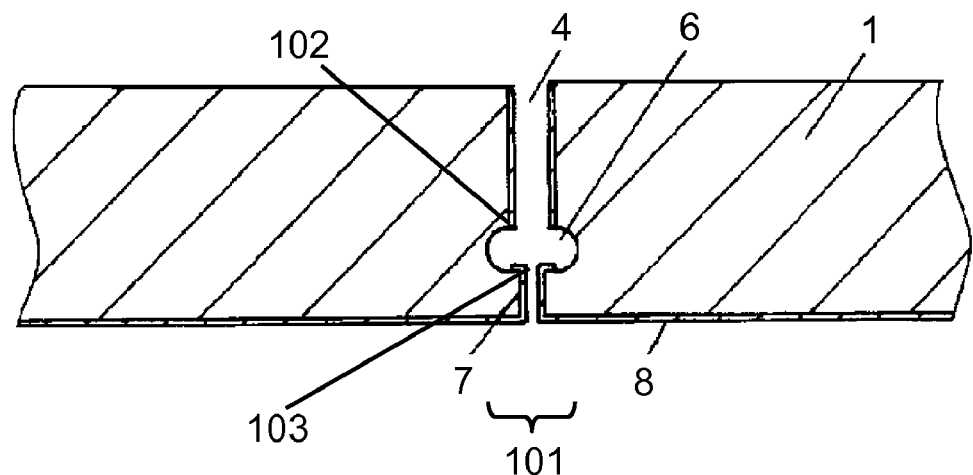
FIG. 3 is an enlarged sectional view of the device in accordance with Embodiment 1.

FIG. 1 is a perspective view of a device for measuring an extracellular potential in accordance with Exemplary Embodiment of the present invention. FIG. 2 is a sectional view of the device. FIG. 3 is an enlarged sectional view of the device.

The measuring device includes substrate 1 made of silicon having well 2 formed therein. Bottom 3 of well 2 has plural trap-holes 101 formed therein for retaining cells. Each of the trap-holes 101 includes first opening 4, hollow section 6, and second opening 5 aligned in this order on a straight line. A diameter of first opening 4 is smaller than a maximum diameter of hollow section 6, and greater than a diameter of second opening 5.

Respective specific sizes of those portions are optimally determined according to a size of a test cell. For a test cell having a diameter of 25 μm, for instance, first opening 4 has a diameter of 20 μm, which is smaller than 25 μm, and hollow section 6 has the maximum diameter of 35 μm, which is greater than that of the cell. A diameter of second opening 5 is determined to be about 10 μm, which is smaller than that of the test cell. A test cell generally has a diameter ranging from several micrometers to several tens of micrometers. Therefore, the diameter of first opening 4 is preferably 10-50 μm, the diameter of second opening 5 is 1-5 μm, and the maximum diameter of hollow section 6 is accordingly determined to be an optimal value between 10 μm and 100 μm.

As shown in FIG. 3, detecting electrode 7 made of gold is formed at least on an inner wall of second opening 5 and a lower part of hollow section 6, and leader electrode 8 made of gold is provided on the lower surface of substrate 1. Electrode 7 is electrically connected to electrode 8 at second opening 5. No conductive material is provided on an upper part of hollow section 6, so that detecting electrode 7 is electrically insulated from well 2.

Figure 4:
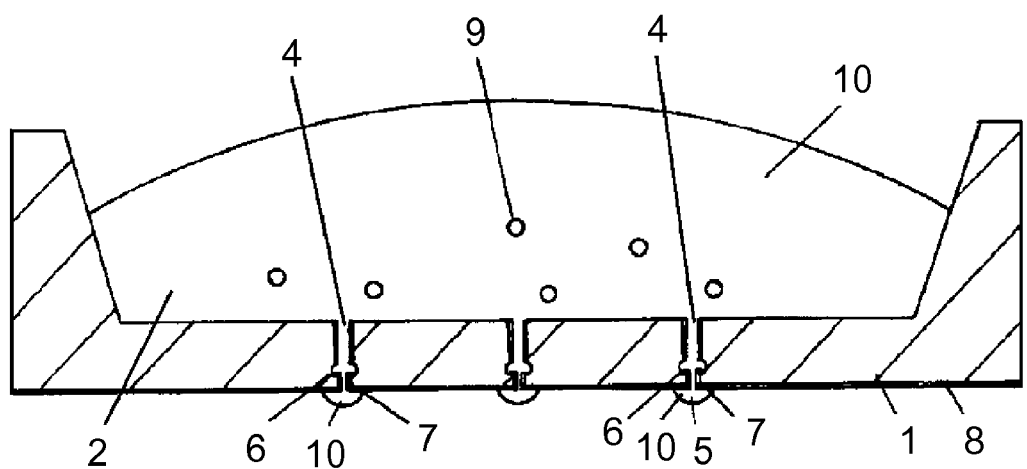
FIG. 4 is a sectional view of the device in accordance with Embodiment 1 for illustrating its usage.

Usage of the measuring device will be described below. FIG. 4 is a sectional view of the device having well 2 containing test cell 9 and culture solution 10 put thereinto. FIG. 5 through FIG. 9 are enlarged sectional views of first opening 4, second opening 5 and hollow section 6.

Figure 5:
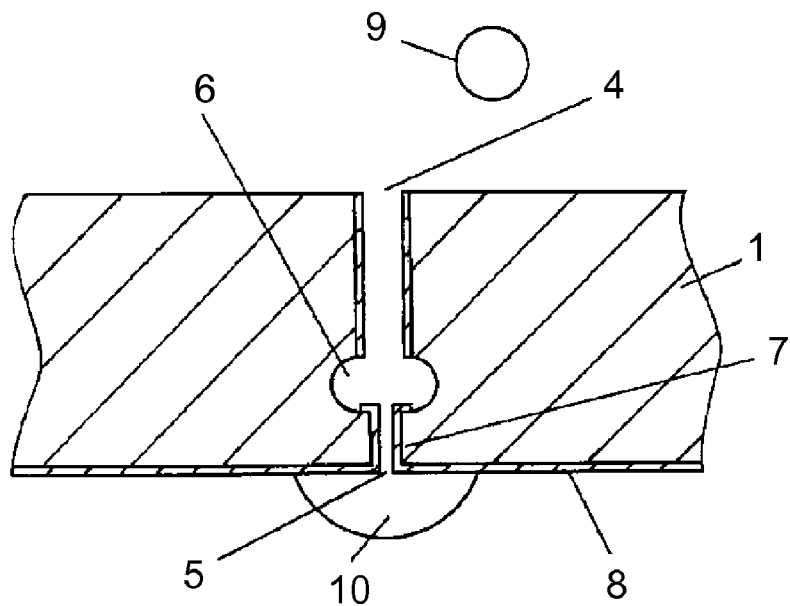
FIG. 5 is an enlarged sectional view of the device in accordance with Embodiment 1.
Figure 6:
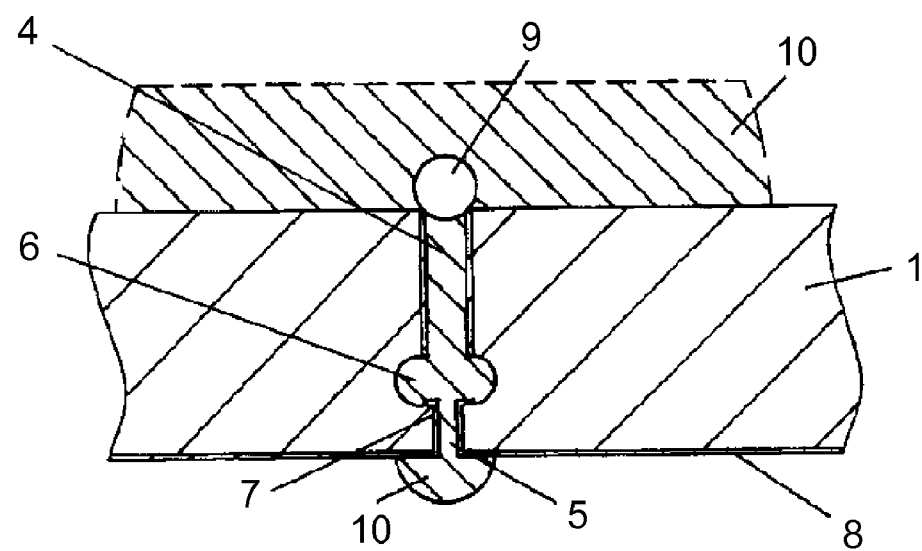
FIG. 6 is an enlarged sectional view of the device in accordance with Embodiment 1.

As shown in FIGS. 4 and 5, just after putting culture solution 10 and test cells 9 into well 2, cells 9 float in solution 10. Not only well 2 but also first opening 4, hollow section 6, and second opening 5 are filled with solution 10, and then, solution overflows from second opening 5. At this moment, as shown in FIG. 6, floating cell 9 is sucked onto first opening 4 by a pressure of solution 10 in well 2. If the pressure is small, solution 10 may be sucked with a suction pump through second opening 5, thus allowing floating cell 9 to be sucked onto first opening 4 more securely.

Figure 7:
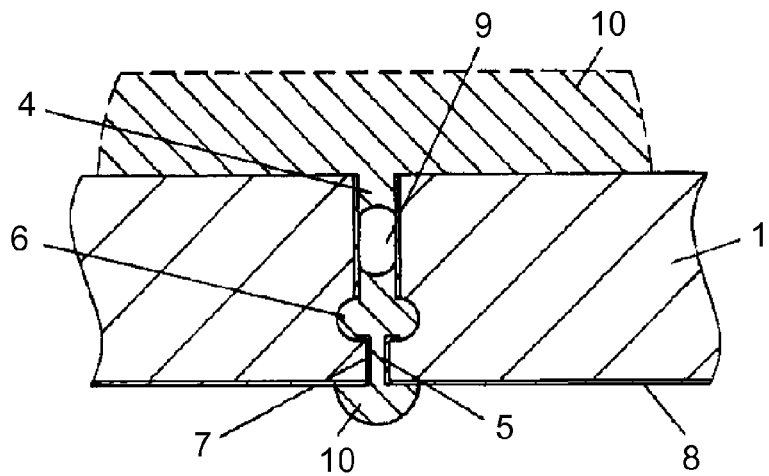
FIG. 7 is an enlarged sectional view of the device in accordance with Embodiment 1.
Figure 8:
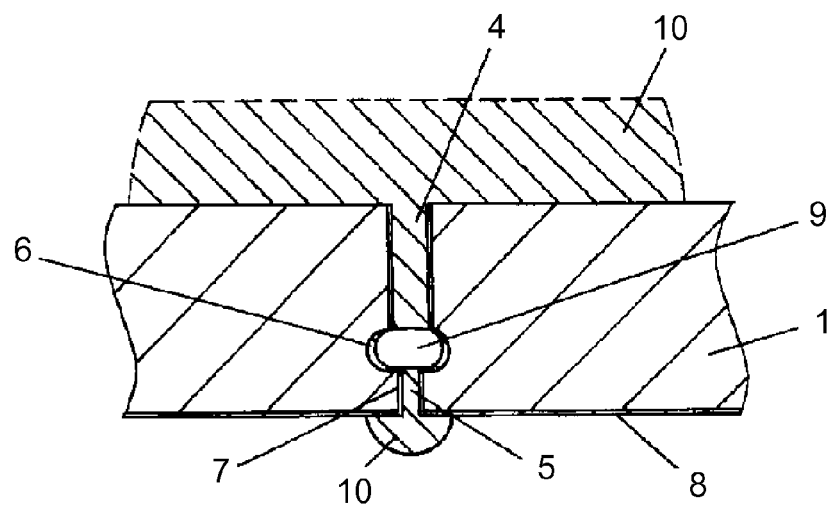
FIG. 8 is an enlarged sectional view of the device in accordance with Embodiment 1.

Since the diameter of first opening 4 is smaller than that of cell 9, cell 9 receives a resistance when passing through opening 4, as shown in FIG. 7. However, due to being forced by the pressure and the suction, cell 9 can reach hollow section 6, while the cell deforms. As shown in FIG. 8, cell 9 reaching hollow section 6 still receives the pressure of culture solution 10 from well 2 even if the suction stops. Since cell 9 has the diameter greater than that of opening 4, and since first opening 4 is provided substantially vertically, cell 9 does not return to well 2 as long as an external force which sucks cell 9 is not applied from well 2. Thus, cell 9 is retained in hollow section 6.

Figure 9:
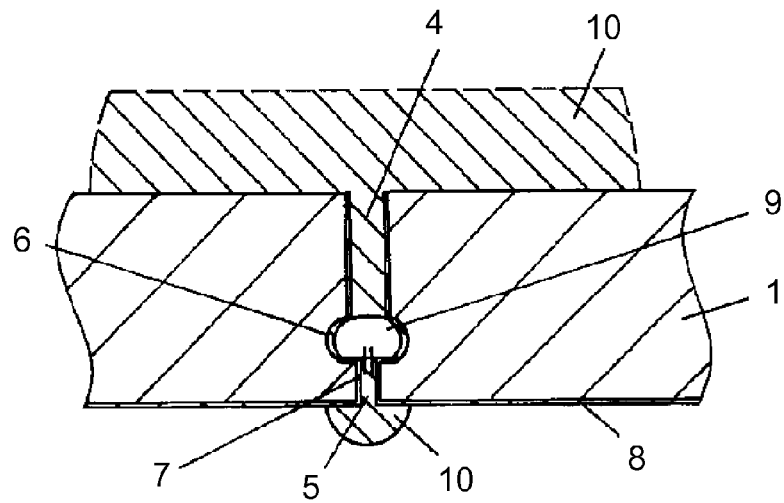
FIG. 9 is an enlarged sectional view of the device in accordance with Embodiment 1.

Hollow section 6 has an oval shape, which has a lateral diameter greater than a vertical diameter, and the vertical diameter is smaller than the diameter of cell 9, as shown in FIGS. 7-9. These dimensions allow cell 9 to be held in hollow section 6 without fail. At that moment, chemicals (not shown) are doped into culture solution 10 in well 2 and permeate into solution 10. The chemicals activate test cell 9, as shown in FIG. 9, and have the cell 9 generate an electric signal at second opening 5. The electric signal changes an electric potential of solution 10 at second opening 5. This change of the potential is detected by detecting electrode 7 and leader electrode 8 which both contact solution 10.

As such, the measuring device in accordance with Embodiment 1 includes detecting electrode 7 electrically insulated from well 2, and hollow section 6 retains test cell 9 securely. In other words, culture solution 10 at second opening 5 is electrically insulated from solution 10 in well 2. Therefore, the electric signal generated through the activities of the cell does not leak to solution 10 in well 2, and is detected by detecting electrode 7 provided on second opening 5.

If any one of the trap holes retains the test cell, an extracellular potential can be measured.

Figure 29:
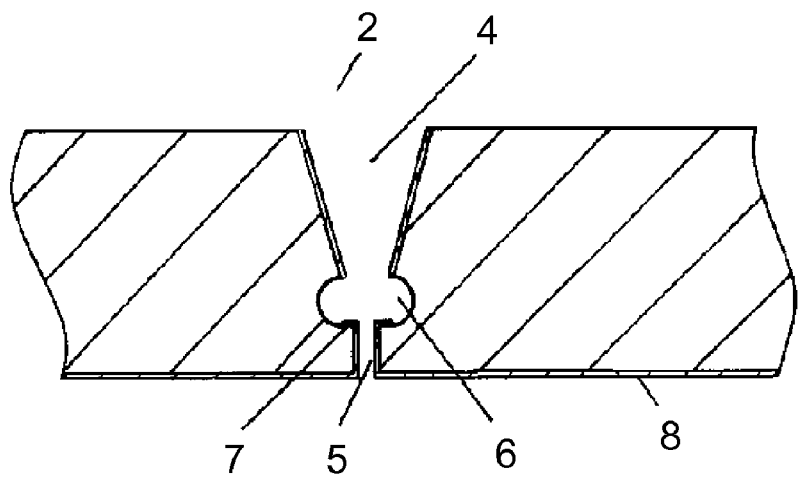
FIG. 29 is a sectional view of another device for measuring an extracellular potential in accordance with Embodiment 1.

First opening 4 may have a tapered shape flaring towards well 2, as shown in FIG. 29. This shape allows test cell 9 to enter into opening 4 from well 2 easily. If a diameter of opening 4 at a boundary of opening 4 against hollow section 6 is smaller than the maximum diameter of hollow section 6, test cell 9 is prevented from returning to well 2. Test cell 9 is thus trapped in hollow section 6, and the measuring device has a high retention rate of the cell. In this device, the diameter of hollow section 6 is greater than the diameter of first opening 4 at the boundary against hollow section 6, and the diameter of first opening 4 at the boundary against hollow section 6 is greater than the diameter of second opening 5.

A diameter of first opening 4 at a boundary against well 2 may be smaller than twice the diameter of the test cell, thus preventing plural cells from entering into opening 4 simultaneously and from clogging opening 4.

In the measuring device in accordance with Embodiment 1, test cell 9 cannot return to well 2 after entering trap hole 101. Thus, test cell 9, a somatic sample, contaminates well 2 and trap-hole 101 during the measurement. The measuring device may be disposable and not re-used, thus preventing cell 9 from being removed.

Next, processes for manufacturing the measuring device in accordance with Embodiment 1 will be described below. FIG. 10 through FIG. 19 are sectional views of the measuring device which illustrate the processes.

Figure 10:
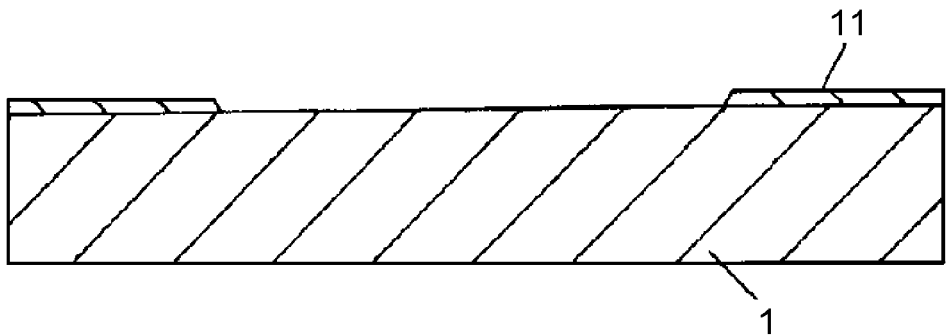
FIG. 10 is a sectional view of the device in accordance with Embodiment 1 for illustrating a method of manufacturing the device.
Figure 11:
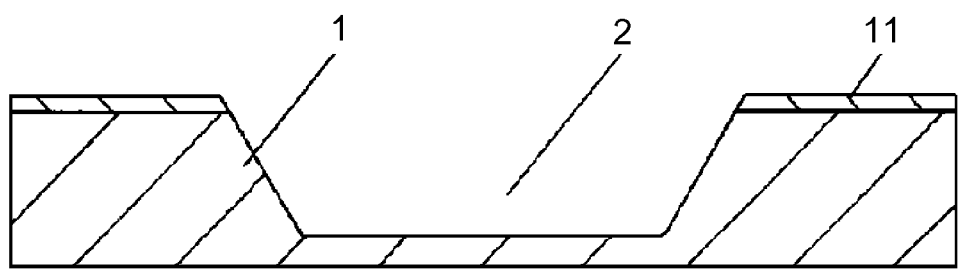
FIG. 11 is a sectional view of the device in accordance with Embodiment. 1 for illustrating the method.

First, as shown in FIG. 10, resist mask 11 is provided on silicon substrate 1 by a photo-lithography method in order to form well 2. Then, as shown in FIG. 11, well 2 is formed by etching substrate 1 up to a predetermined depth by a wet etching method or a dry etching method. The wet etching method may employ KOH or tetramethyl ammonium hydroxide (TMAH) as an etching solution. The dry etching method may employ $SF_6$ or $CF_4$ as an etching gas.

Figure 12:
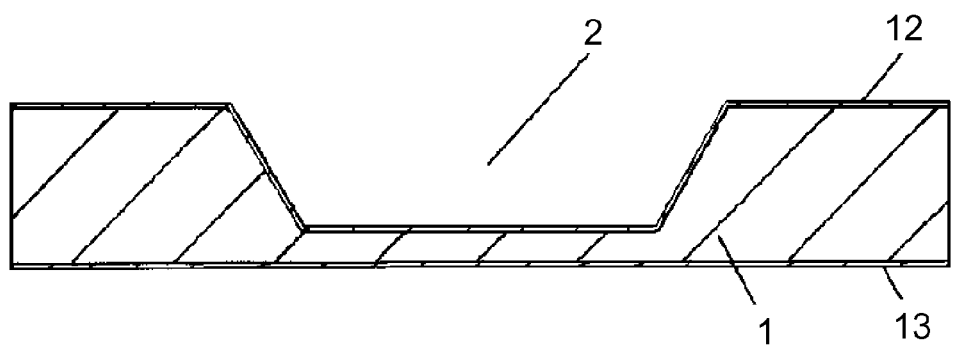
FIG. 12 is a sectional view of the device in accordance with Embodiment. 1 for illustrating the method.

Then, as shown in FIG. 12, resist mask 12 for forming first opening 4 is provided on a bottom of well 2, and resist mask 13 for forming second opening 5 is provided on a lower surface of silicon substrate 1. The diameters of openings 4 and 5 are determined according to a size of test cell 9. The diameter of first opening 4 is greater than that of second opening 5.

Figure 13:
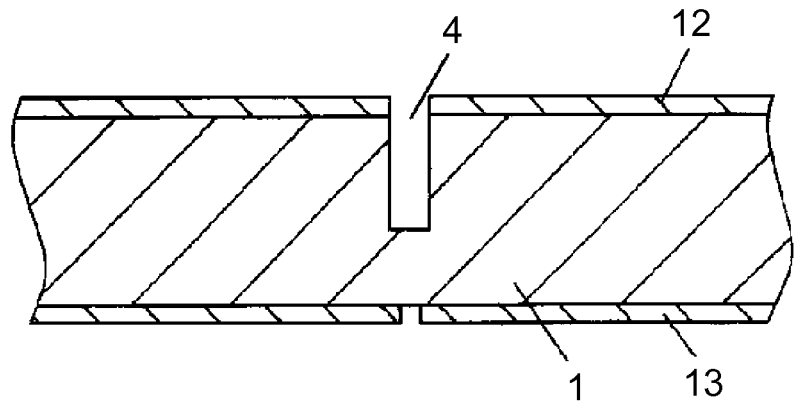
FIG. 13 is an enlarged sectional of the device in accordance with Embodiment 1 for illustrating the method.

Next, as shown in FIG. 13, substrate 1 is etched from well 2 up to a predetermined depth for forming first opening 4. Substrate 1 may be etched preferably by a dry etching method employing both etching-accelerator gas and etching-suppressor gas. The accelerator gas may be $SF_6$ or $CF_4$ accelerating an etching of silicon not only depth wise but also lateral wise. The gas may be mixed with $CHF_3$ or $C_4F_8$, which suppresses the etching, and forms a protective film made of polymer of $CF_2$ on the wall of the opening, thus allowing the substrate to be etched only below the mask.

In order to etch the substrate in a vertical direction, the following steps are repeated. That is, the substrate is etched a little with the etching-accelerator gas, and then, the protective film is formed with the etching-suppressor gas. These steps form the opening substantially vertically. According to an experiment, first opening 4 having a diameter of 20 μm is formed by the following steps. $SF_6$ flows at a rate of 130 sccm to generate plasma for 13 seconds, thereby etching substrate 1 by 1 μm. Then, $C_4F_8$ flows at a rate of 85 sccm to generate plasma for 7 seconds, thereby forming the protective film having a thickness of 0.01 μm. The steps of etching substrate 1 and forming the protective film are repeated about 60 times, thereby forming a substantially vertical opening having a depth of 60 μm.

The protective film is formed not only on the wall of first opening 4 but also on the bottom with the etching-suppressor gas. The protective film formed on the bottom can be removed by the etching-accelerator gas more easily than the protective film on the wall, thus allowing the substrate to be etched only downward.

First opening 4 is thus formed, while the protective film is formed with the etching-suppressor gas. After first opening 4 is formed, the protective film is formed on the wall of opening 4. The film protects the wall of opening 4 from damage during the forming of hollow section 6.

Figure 14:
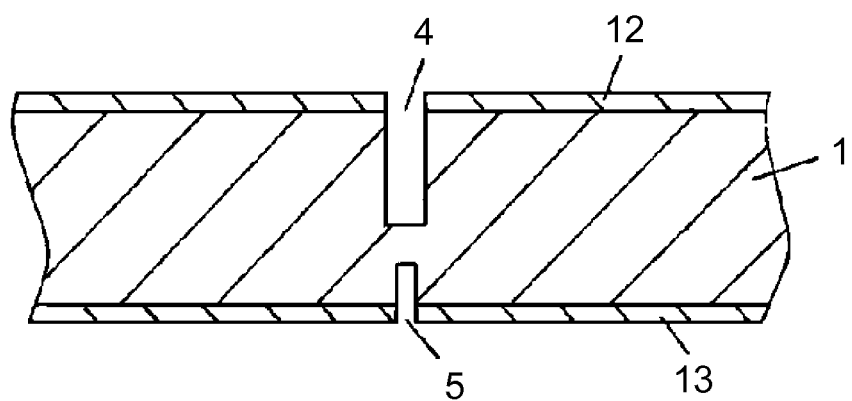
FIG. 14 is an enlarged sectional of the device in accordance with Embodiment 1 for illustrating the method.

Then, as shown in FIG. 14, substrate 1 is etched from its lower surface in order to form second opening 5. The etching-accelerator gas and the etching-suppressor gas are alternately used similarly to the forming of first opening 4, thus allowing the wall of second opening 5 to be formed substantially vertically.

Further, the protective film is formed with the etching-suppressor gas, similarly to the forming of first opening 4, to complete the forming of second opening 5. The wall of opening 5 is thus protected by the film securely, thus being prevented from being damaged when hollow section 6 is formed in later processes.

Figure 15:
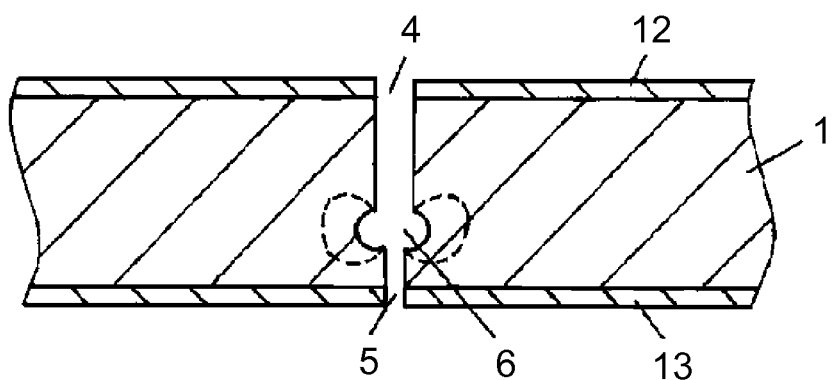
FIG. 15 is an enlarged sectional of the device in accordance with Embodiment 1 for illustrating the method.

Next, as shown in FIG. 15, substrate 1 is etched from first opening 4 only with the etching-suppressor gas. The protective film is provided on the wall of opening 4 at the previous process, thus allowing the substrate to be etched downward without damage to the wall. A portion which is newly etched does not have a protective film thereon, thus being etched also laterally. This etching forms hollow section 6 which is provided between first opening 4 and second opening 5 and is wider than first opening 4, as shown in FIG. 15. An appropriate amount of substrate 1 is etched to have hollow section 6 shaped in the oval having the lateral diameter greater than the vertical diameter.

After hollow section 6 communicates with second opening 5, the protective film is still formed on the wall of opening 5.

The film protects the wall of opening 6 from damage even though substrate 1 is being etched for a while until hollow section 6 has a predetermined size. If the substrate is excessively etched, hollow section 6 expands not only in a lateral direction but also in all directions, as denoted by dotted lines shown in FIG. 15. The substrate is finished appropriately to etch.

The etching accelerator gas used in the above-described etching may include $SF_6$ or $CF_4$ and, however, preferably includes $XeF_2$ which hardly etches the protective film. The gas of $XeF_2$ forms hollow section 6 with little damage on the wall. The gas of $XeF_2$, however, needs a long time to etch the protective film on the bottom of the opening formed in the previous process. In order to overcome this problem, the protective film on the bottom may be etched with the gas, such as $SF_6$, $CF_4$ or Ar, before the gas of $XeF_2$ is used.

According to Embodiment 1, first opening 4, second opening 5 and hollow section 6 are formed in this order. However, second opening 5, first opening 4 and hollow section 6 may be formed in this order, or first opening 4, hollow section 6 and second opening 5 may formed in this order. Hollow section 6 may be etched from second opening 5. In this case, the substrate is etched carefully to allow hollow section 6 to be greater than first opening 4.

Figure 16:
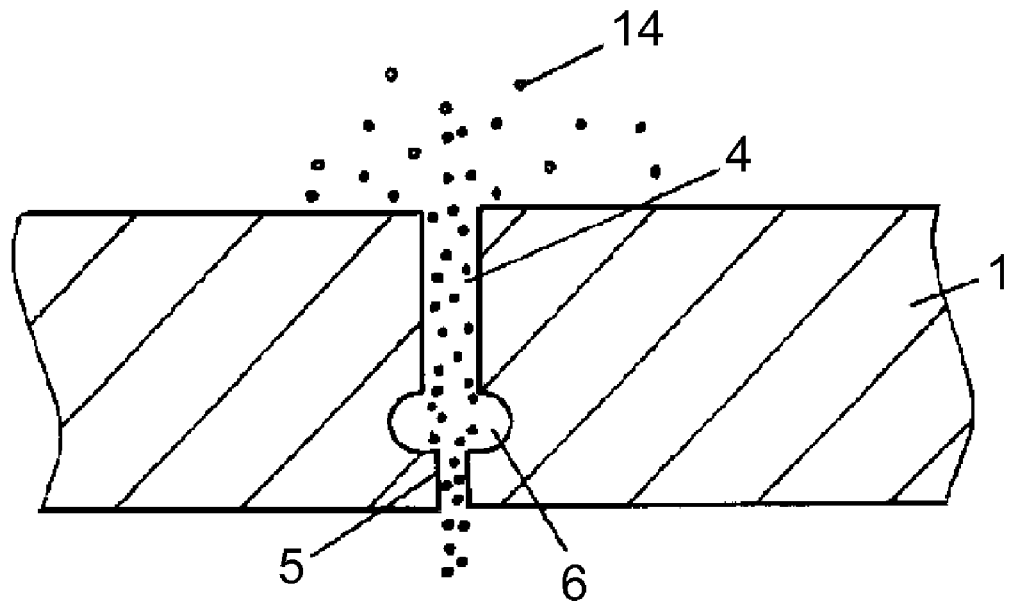
FIG. 16 is an enlarged sectional of the device in accordance with Embodiment 1 for illustrating the method.
Figure 17:
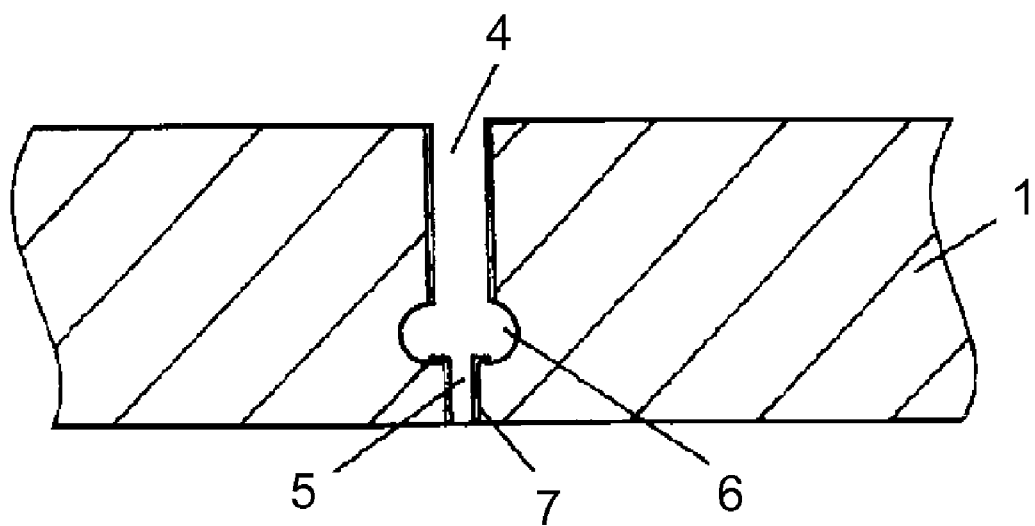
FIG. 17 is an enlarged sectional of the device in accordance with Embodiment 1 for illustrating the method.

Next, as shown in FIG. 16, all the resist masks are removed, and then, gold particles 14 are attached onto the wall by a vapor deposition method, thereby forming detecting electrode 7. In this process, gold particles 14 are discharged from a target of first opening 4. Particles 14 discharged from the target run straight, thus passing through first opening 4. Then, as shown in FIG. 17, the particles deposit only on an inner wall of opening 4, a lower part of hollow section 6, and an inner wall of opening 5. In other words, detecting electrode 7 is formed only on the inner wall of second opening 5 and the lower part of hollow section 6.

Figure 18:
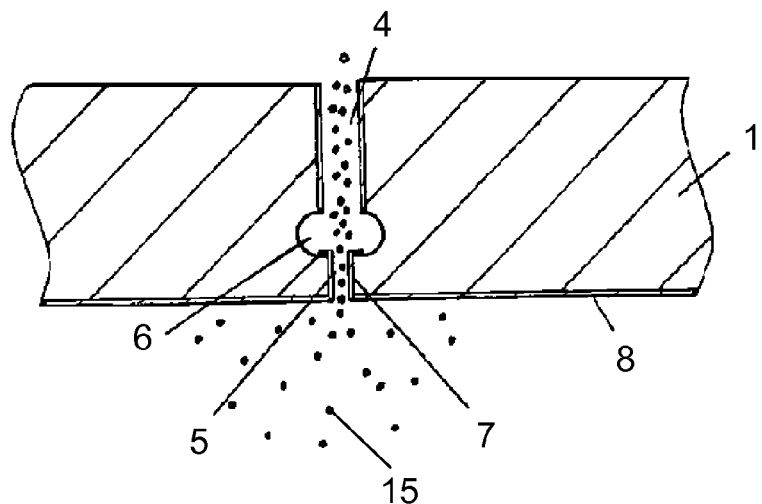
FIG. 18 is an enlarged sectional of the device in accordance with Embodiment 1 for illustrating the method.
Figure 19:
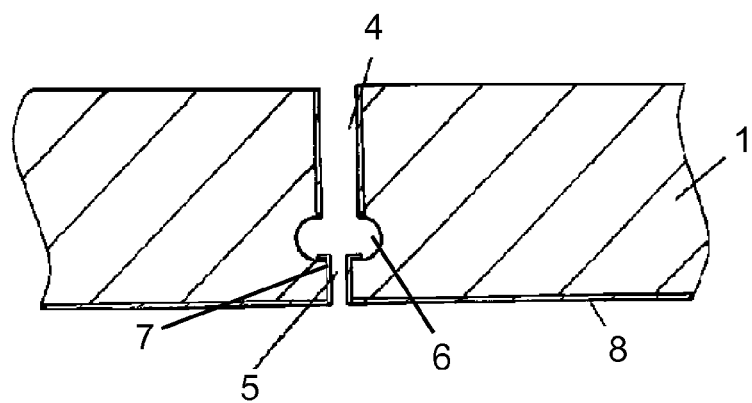
FIG. 19 is an enlarged sectional of the device in accordance with Embodiment 1 for illustrating the method.

Then, as shown in FIG. 18, leading electrode 8 made from gold is formed on a surface of the substrate at second opening 5. Since second opening 5 has a diameter smaller than that of first opening 4, gold particles 15 run straight and deposit only on the inner wall of opening 5 and a portion of the inner wall of opening 4. As shown in FIG. 19, detecting electrode 7 formed on the lower part of hollow section 6 and the inner wall of second opening 5 is electrically insulated from the gold provided on the inner wall of first opening 4. In order to attach the gold securely to substrate 1, a buffer layer of chrome or titan may be provided on substrate 1, and the gold can be attached on the buffer layer. In order to avoid depositing the gold on the bottom of well 2, the gold is deposited before resist mask 12, which has been disposed for forming first opening 4, is removed. The mask prevents the gold from depositing on the bottom of well 2 after resist mask 12 is removed. The gold may be deposited by a sputtering instead of the vapor-deposition.

The second openings of the trap-holes have conductors formed on the walls of the openings, and the conductors are short-circuited with each other at the lower surface below the well. This structure creates a parallel connection of electric potential changes around the test cells held in the trap-holes, so that the change in the electric potential of each test cell may be detected even if each electric potential change is small.

The manufacturing method in accordance with Embodiment 1 allows silicon substrate 1 to have well 2 and first opening 4, second opening 5, and hollow section 6 which retains the test cell securely, thus providing a reliable device for measuring an extracellular potential.

According to Embodiment 1, substrate 1 is made from silicon and however, may be made of material which can be dry-etched easily to be etched straight and laterally through switching etching gases. For instance, glass and quartz can be etched in a depth direction with gas, such as $SF_6$ or $CF_4$, and in a lateral direction with gas of HF.

Figure 20:
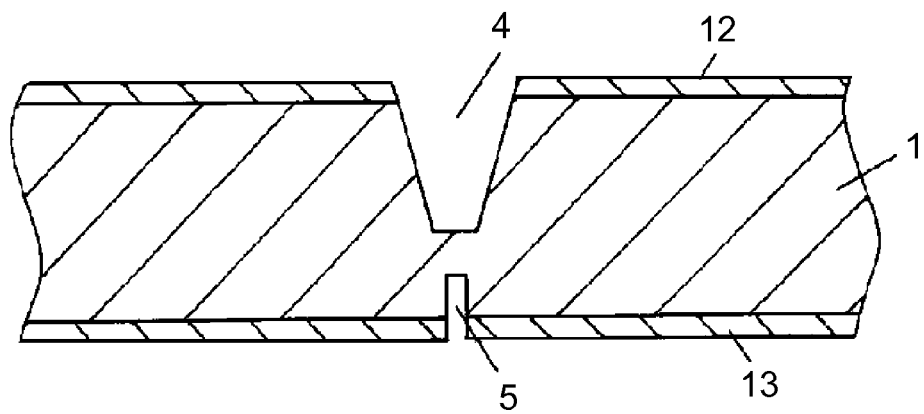
FIG. 20 is an enlarged sectional view of the device in accordance with Embodiment 1 for illustrating another method of manufacturing the device.
Figure 21:
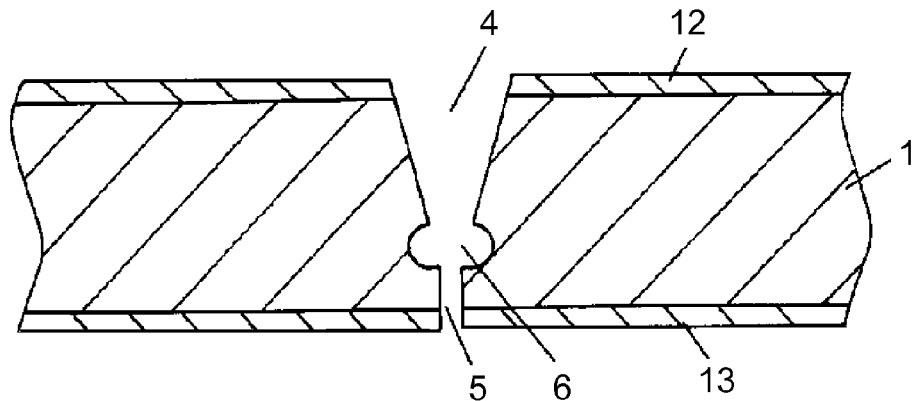
FIG. 21 is an enlarged sectional view of the device in accordance with Embodiment 1 for illustrating another method.

According to Embodiment 1, first opening 4 is provided substantially perpendicularly to the bottom of well 2. First opening 4, upon having a tapered shape having a diameter at well 2 greater than that at hollow section 6, may be formed by the following processes. When the gas including the etching-accelerator gas and the etching suppressor gas mixed is used, a concentration of the etching-accelerator gas is reduced according to proceeding of the etching from well 2 toward hollow section 6. This operation allows the wall of opening 4 to taper, as shown in FIG. 20. This tapered shape allows test cell 9 to enter into opening 4 easily, and prevents cell 9 once trapped in hollow section 6 from return to well 2 easily.

Figure 22:
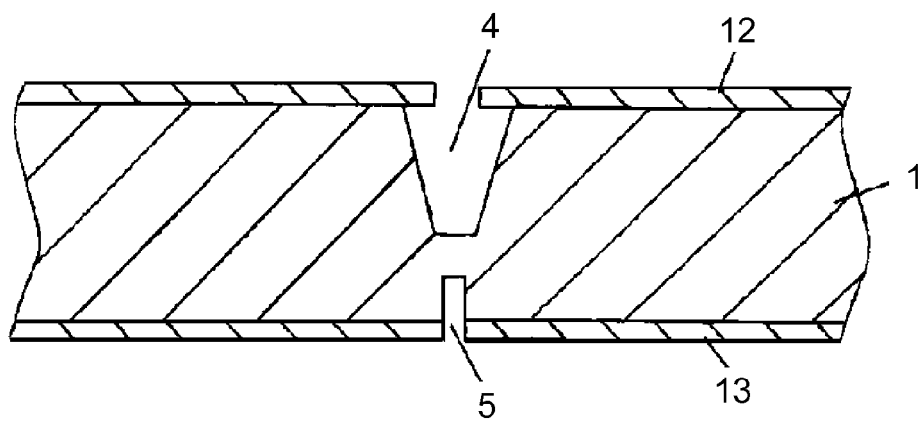
FIG. 22 is an enlarged sectional view of the device in accordance with Embodiment 1 for illustrating another method.

In order to make the wall of opening 4 taper, substrate 1 may be etched with only the etching-accelerator gas. In this case, as shown in FIG. 22, the diameter of opening 4 at the boundary against well 2 becomes greater than the diameter defined by resist mask 12. Therefore, the diameter defined by resist mark 12 is determined in advance in order to get an optimum taper shape.

According to Embodiment 1, the relation among the diameters of openings 4 and 5 and hollow section 6 is described. As shown in FIG. 3, connecting portion 102, which is a border between opening 4 and hollow section 6, has a diameter smaller than the maximum diameter of hollow section 6. Connecting portion 103, which is a border between opening 5 and hollow section 6, has a diameter smaller than that of connecting portion 102. This arrangement provides advantages identical to those discussed above.

Exemplary Embodiment 2

Figure 23:
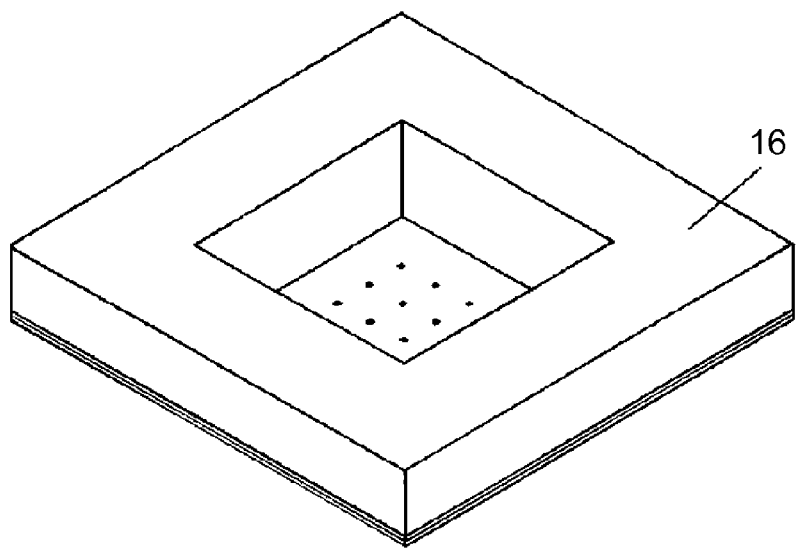
FIG. 23 is a perspective view of a device for measuring an extracellular potential in accordance with Exemplary Embodiment 2 of the invention.
Figure 24:
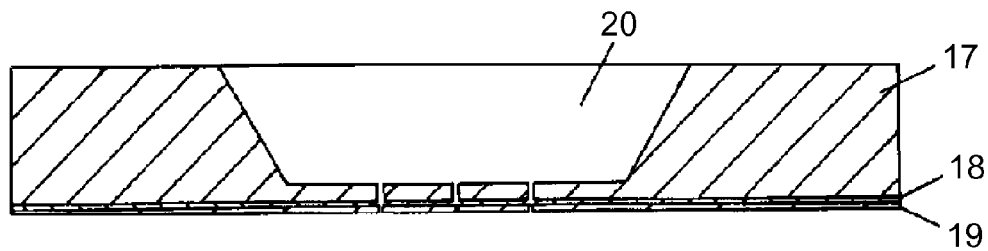
FIG. 24 is a sectional view of the device in accordance with Embodiment 2.
Figure 25:
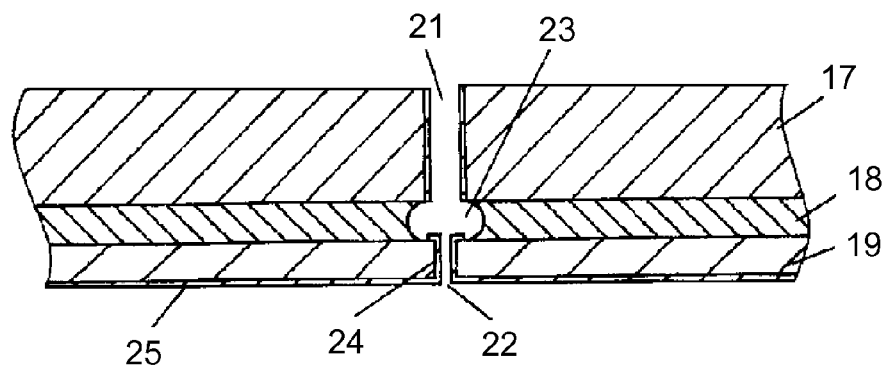
FIG. 25 is an enlarged sectional view of the device in accordance with Embodiment 2.

FIG. 23 is a perspective view of a device for measuring an extracellular potential in accordance with Exemplary Embodiment 2 of the present invention. FIG. 24 is a sectional view of the device. FIG. 25 is an enlarged sectional view of the device. Substrate 16 is formed by stacking first silicon layer 17, silicon dioxide layer 18, and second silicon layer 19, differently from a device of Embodiment 1. First opening 21, second opening 22, and hollow section 23 are formed in first silicon layer 17, second silicon layer 19, and silicon dioxide layer 18, respectively.

Detecting electrode 24 is formed only on an inner wall of second opening 22 and a lower portion of hollow section 23, and leading electrode 25 is formed on a lower surface of substrate 16. Detecting electrode 24 is electrically connected to leading electrode 25 around second opening 22.

An operation of the device discussed above is identical to that of Embodiment 1, and the description thereof is thus omitted. Silicon dioxide layer 18 between first silicon layer 17 and second silicon layer 19 increases electrical insulation between the layers. Therefore, an electric signal generated by activity of a cell at second opening 22 can be detected securely by detecting electrode 24, and the signal does not leak to first opening 21.

Processes for manufacturing the device in accordance with Embodiment 2 are described below. A description of processes identical to those of Embodiment 1 is omitted, and only processes for forming first opening 21, second opening 22, and hollow section 23 will be described below. The substrate includes the silicon layer, the silicon dioxide layer, and the silicon layer stacked in this order, which is available in market as an SOI substrate, and is not thus explained.

Figure 26:
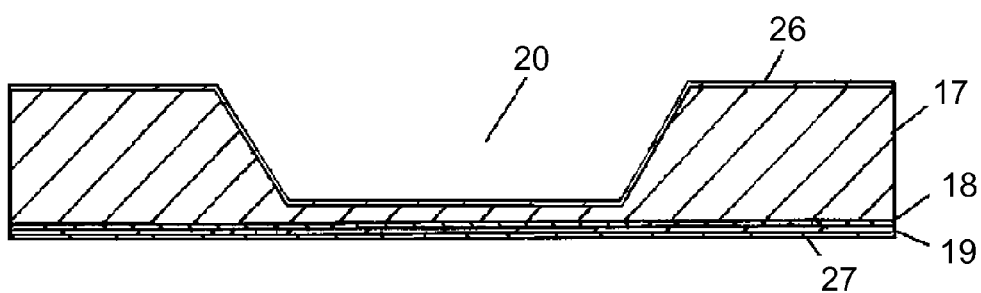
FIG. 26 is a sectional view of the device in accordance with Embodiment 2 for illustrating a method of manufacturing the device.
Figure 27:
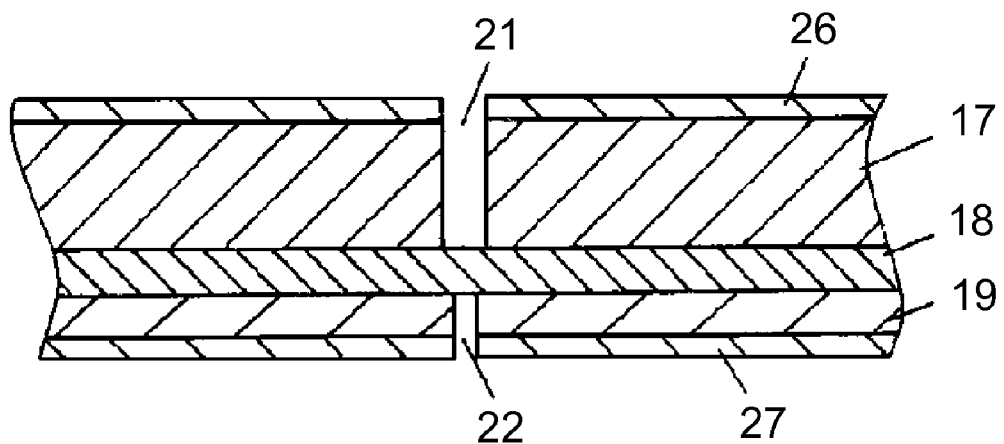
FIG. 27 is a sectional view of the device in accordance with Embodiment 2 for illustrating the method.

First, well 20 is formed in first silicon layer 17, and then, as shown in FIG. 26, resist masks 26 and 27 is provided in order to form first opening 21 and second opening 22. Next, as shown in FIG. 27, layers 17 and 19 are dry-etched from a bottom of well 20 and a lower surface of substrate 16, respectively, so that respective walls of the openings become perpendicular to the bottom of well 20, and the openings reach silicon dioxide layer 18. The substrate is etched, similarly to Embodiment 1, with etching-accelerator gas for facilitating the etching and etching-suppressor gas for suppressing the etching. In order to form openings 21 and 22, layers 17 and 19 are etched until the openings reach silicon dioxide layer 18. This etching requires no monitoring of an etching time for obtaining a predetermined depth.

Figure 28:
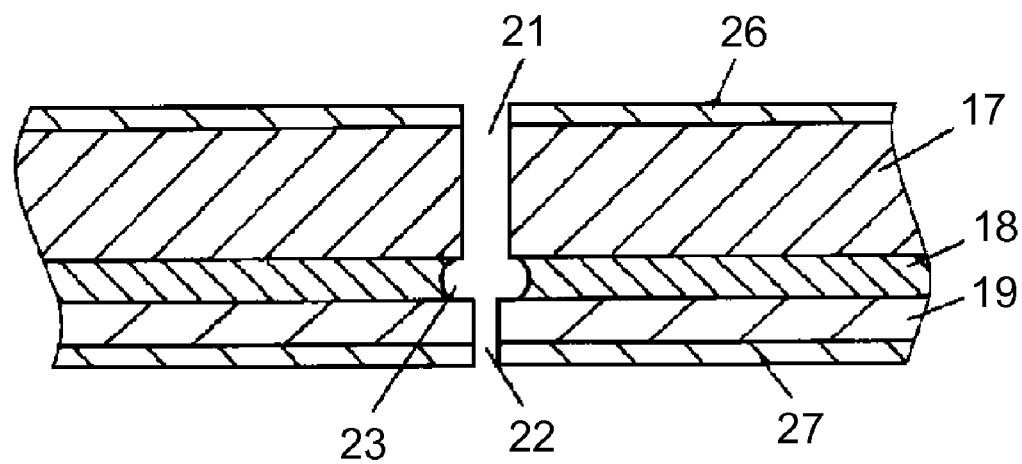
FIG. 28 is a sectional view of the device in accordance with Embodiment 2 for illustrating the method.

Next, the substrate is dipped into solution of HF, which mainly etches silicon dioxide layer 18 and etches layer 17 and 19 little to form hollow section 23, as shown in FIG. 28. Layer 18 is etched until hollow section 23 has a necessary lateral diameter. Then, similarly to Embodiment 1, detecting electrode 24 and leading electrode 25 are formed. Layer 18 may be etched with plasma using HF gas, which etches the silicon layers little but etches mainly silicon dioxide layer 18 similarly to the HF solution. An etching of Embodiment 1, an etching of excessively long time does not make the hollow section oval; however, the method of Embodiment 2 overcomes this problem.

In substrate 16 including two kinds of layers, namely, silicon and silicon dioxide layers, the depth of second opening 22 and the height of hollow section 23 are determined in advance, thus allowing the device to be manufactured easily. Silicon dioxide layer 18 completely isolates first opening 21 electrically from second opening 22, thus providing a reliable measuring device.

According to Embodiment 2, substrate 16 includes three layers, i.e., first silicon layer 17, silicon dioxide layer 18, and second silicon layer 19. However, the substrate may include four layers, i.e., a silicon layer, a silicon dioxide layer, a silicon layer, and a silicon dioxide layer, or more than four layers.

Substrate 16 is formed by stacking the silicon layer, the silicon dioxide layer, and the silicon layer in this order. However, a substrate formed by stacking a silicon dioxide layer, a silicon layer, and a silicon dioxide layer in this order may provide the device. Substrate 16 may be made of not only the combination of silicon and silicon dioxide, but also other combinations, such as silicon and glass, aluminum and aluminum oxide, or glass and resin. Substrate 16 may be made of three materials instead of the two materials, and may include layers of materials different from each other. Such substrates provide advantages similar to those discussed above.

Similarly to Embodiment 1, as shown in FIG. 3, a first connection section at a border between the first opening and the hollow section has a diameter smaller than the maximum diameter of the hollow section, and a second connection section at a border between the second opening and the hollow section has a diameter smaller than that of the first connection section. This structure provides advantages similar to those of Embodiment 2.

Exemplary Embodiment 3

Figure 30:
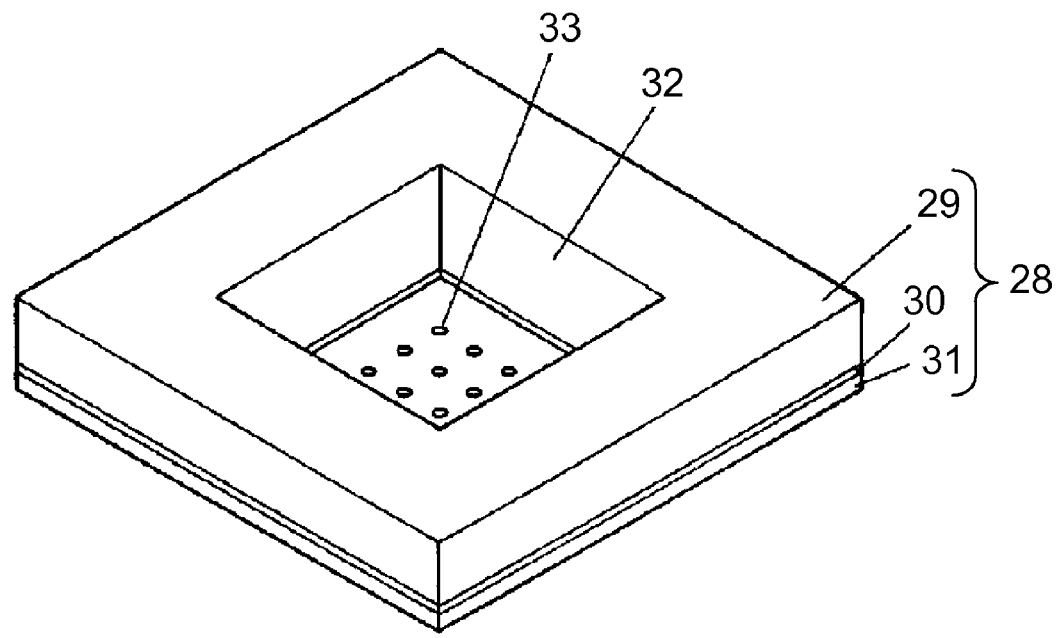
FIG. 30 is a perspective view of the device for measuring an extracellular potential in accordance with Exemplary Embodiment 3 of the invention.
Figure 31A:
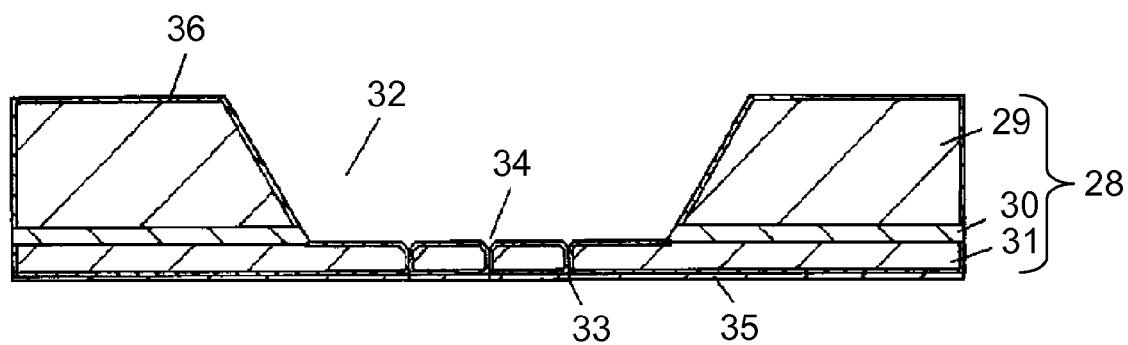
FIG. 31A is a sectional view of the device in accordance with Embodiment 3.
Figure 31B:
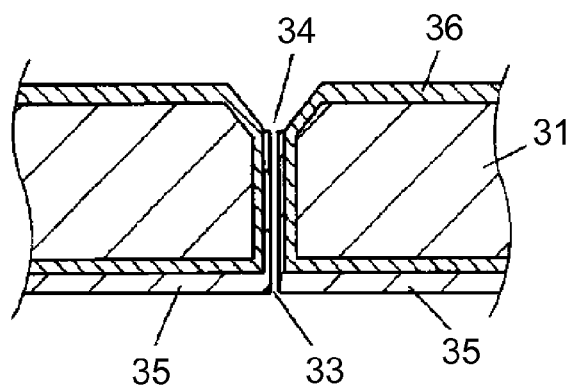
FIG. 31B is an enlarged sectional view of the device in accordance with Embodiment 3.
Figure 32:
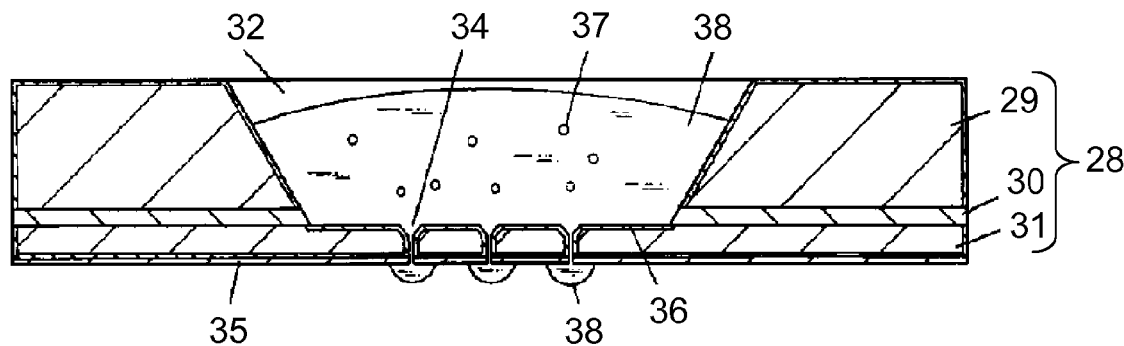
FIG. 32 is a sectional view of the device in accordance with Embodiment 3 for illustrating an operation of the device.
Figure 33:
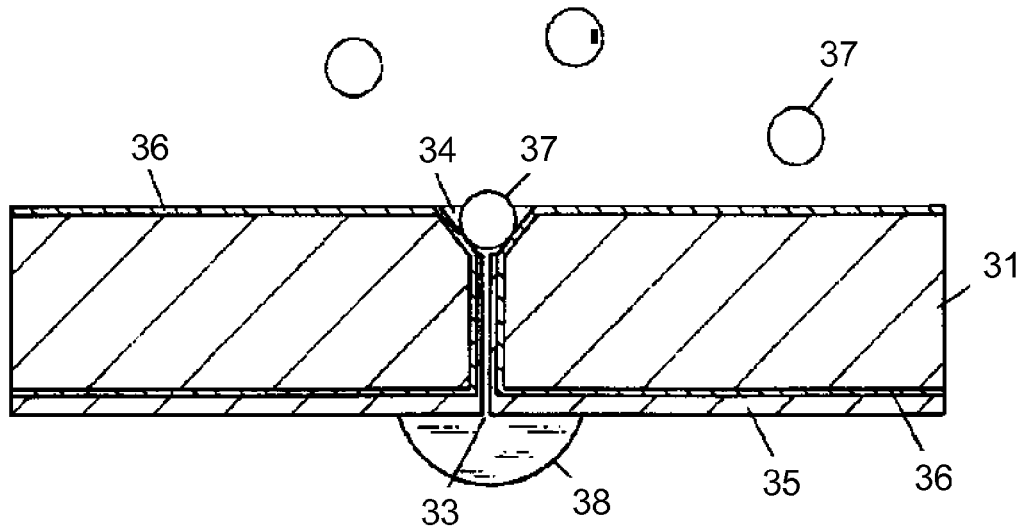
FIG. 33 is an enlarged sectional view of the device in accordance with Embodiment 3.
Figure 34:
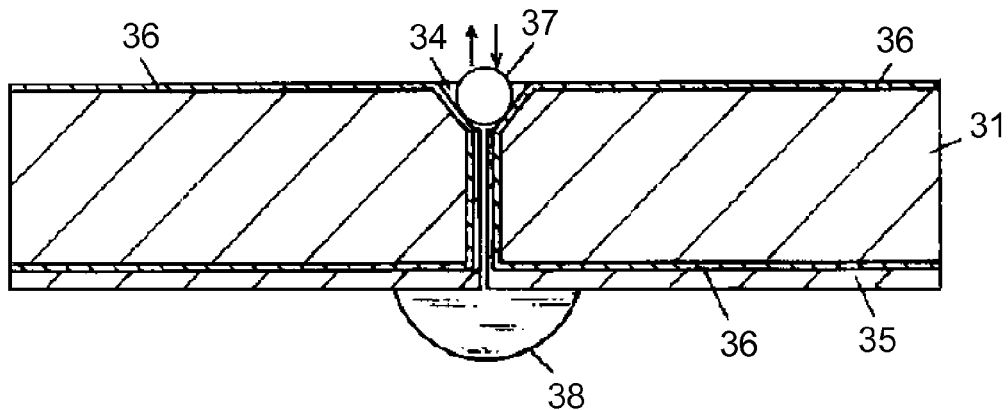
FIG. 34 is an enlarged sectional view of the device in accordance with Embodiment 3.

FIG. 30 is a perspective view of a device for measuring an extracellular potential in accordance with Exemplary Embodiment 3 of the present invention. FIGS. 31A, 31B and 32 are sectional views of the device. FIGS. 33 and 34 are enlarged sectional views of the device. FIG. 35 through FIG. 42 are sectional views of the device for illustrating a method of manufacturing the device.

As shown in FIG. 30 through FIG. 32, substrate 28 has a laminated structure including base 29 made of silicon, intermediate layer 30 made of silicon dioxide, and thin plate 31 made of silicon. Base 29 has well 32 therein for accommodating sample solution including test cells. Well 32 is used for mixing test cells 37 and culture solution with chemicals. Further, thin plate 31 forming the bottom of well 32 has through-holes 33 therein. Well 32 has pockets 34 formed at holes 33, and thus, a diameter of hole 33 at well 32 is greater than a diameter of hole 33 at a lower surface of substrate 28.

Diameters of through-holes 33 and pockets 34 may be determined according to a size and characteristics of test cell 37. For the cell 37 having a diameter of 10 μm, the pocket 34 having a diameter ranging from 10 μm to 20 μm and the hole 33 having a diameter smaller than 5 μm are suitable.

According to Embodiment 3, an inner wall of pocket 34 has a conical shape having its bottom towards well 32.

Insulator 36 made from silicon dioxide is provided on the inner wall and the bottom of well 32, the inner wall of through-hole 33, the inner wall of pocket 34, and the lower surface of thin plate 31. Detecting electrodes 35 made mainly of gold are provided on a portion of insulator 36 on the inner wall of hole 32 and the outside of thin plate 31.

The cell generally has a diameter of 5 μm-20 μm, and thus, an opening of pocket 34 preferably has a diameter of 10 μm-100 μm, and an opening of hole 33 has a diameter of 1 μm-10 μm. The device discussed above can measure an extracellular potential, i.e., a physico-chemical change generated by the cell by the following operation described below with reference to figures.

FIG. 32 is a sectional view of well 32 having test cell 37 and culture solution 38 put therein. FIGS. 33 and 34 are enlarged sectional views of an essential portion including through-hole 33 and pocket 34. As shown in FIG. 32, just after culture solution 38 and test cell 37 are input in well 32, cell 37 floats in solution 38. Well 32 is filled with solution 38 as well as pocket 34 and hole 33 are filled with solution 38, and then, solution 38 overflows to the lower surface of well 32. As shown in FIG. 33, this flow allows floating cell 37 to be sucked in pocket 34 by a pressure of solution 38 in well 32. If the pressure is small, solution 38 may be sucked with a suction pump from hole 33 to allow floating cell 37 to be sucked more securely in pocket 34.

Next, test cell 37 reaching pocket 34 receives a pressure by suction from hole 33 or by culture solution 38 from well 32, thus being retained in pocket 34, as shown in FIG. 33. At this moment, chemicals (not shown) may be doped into culture solution 38 in well 32 to permeate into solution 38. When the chemicals activates test cell 37 due to reaction by ion-exchange, as shown in FIG. 34, an electric signal generated in hole 33 changes an electric potential of a portion of culture solution 38 filled in hole 33. This electric potential change is detected by detecting electrode 35 contacting solution 38.

As described above, pocket 34 provided in the bottom of well 32 allows the device in accordance with Embodiment 3 not to require another well. Test cell 37 and the culture solution can be mixed with the chemicals in well 32. Well 32, pockets 34 provided in the bottom, and through-holes 33 are unitarily formed, thus preventing culture solution 38 from leaking outside well 32 by mistake, and thus allowing the solution to flow to aperture 33.

Insulator 36 of silicon dioxide provided on the inner wall of pocket 34, the inner wall of through-hole 33, the lower surface of thin plate 31, the bottom, and the inner wall of well 32 electrically insulates detecting electrode 35 from well 32. Since pocket 34 has the conical shape having its bottom towards well 32, cell 37 is sucked into pocket 34 and is retained in the pocket stably, thus preventing cell 37 from staying in aperture 33. For instance, if test cell 37 has a diameter of 10 μm, the diameter of pocket 34 at well 32, namely, the bottom of the conical shape is determined to be less than 20 μm, thus plural cells 37 not to enter into pocket 34 at once. Through-hole 33 having a diameter less than 5 μm does not allow cell 37 to pass through hole 33.

As discussed above, test cell 37 can be securely retained in pocket 34 during measuring. A portion of culture solution 38 in hole 33 is electrically insulated from a portion of solution 38 in well 32, thus preventing the electric signal generated by activity of test cell 37 from leaking to the portion of solution 38 in well 32. Therefore, the signal is detected by detecting electrode 35 provided on hole 33. Insulator 36 is necessary when a surface layer of the silicon substrate has a small resistivity. Alternatively, insulator 36 is necessary when the electric signal generated in hole 33 is too weak to be measured due to a little leak of the electric signal to well 32.

Therefore, if the silicon substrate has a large surface resistivity, test cell 37 that is retained assures enough electric insulation. Therefore, when an extracellular potential is large enough not to be influenced by a little leakage of the electric signal, insulator 36 is not necessarily required.

Figure 35:
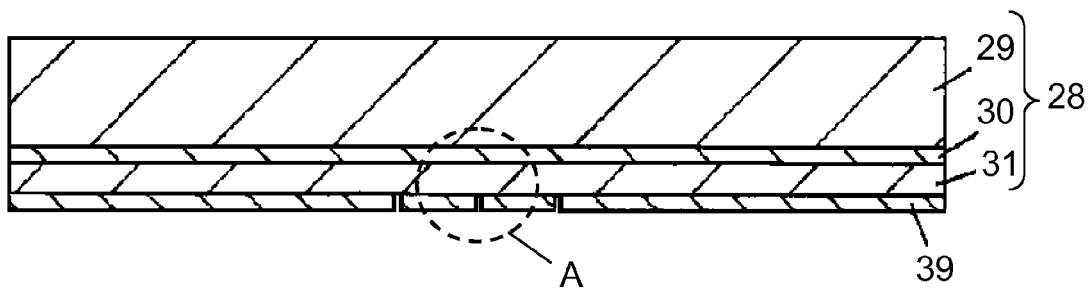
FIG. 35 is a sectional view of the device in accordance with Embodiment 3 for illustrating a method of manufacturing the device.

Next, a method of manufacturing the device in accordance with Embodiment 3 will be described below with reference to FIG. 35 to FIG. 42. First, as shown in FIG. 35, substrate 38 including base 29 made of silicon, intermediate layer 30 made of silicon dioxide, and thin plate 31 made of silicon is prepared. Resist mask 39 is provided on the lower surface of thin plate 31. Substrate 28 may be an SOI substrate, which is often used for manufacturing semiconductor devices. The SOI substrate is available in market, and thus, a method for manufacturing the substrate is not described.

Figure 36:
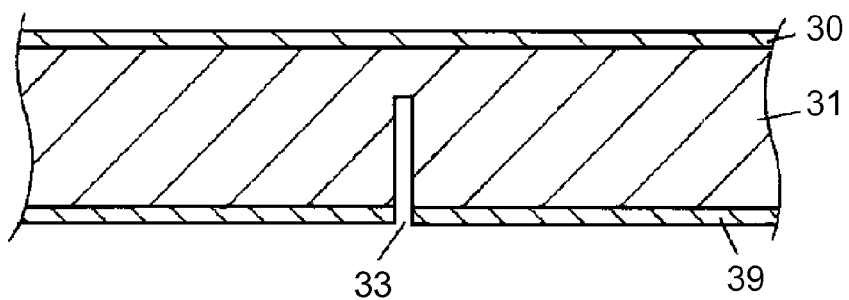
FIG. 36 is an enlarged sectional view of the device in accordance with Embodiment 3 for illustrating the method.

Then, thin plate 31 is dry-etched to form through-hole 33 having a predetermined depth. FIG. 36 is an enlarged of portion A in FIG. 35. It is important that the plate is preferably dry-etched with etching-accelerator gas for facilitating the etching and etching-suppressor gas for suppressing the etching, similarly to Embodiment 1. These gases allow through-hole 33 to be formed only beneath resist mark 39, as shown in FIG. 36.

While substrate 28 is dry-etched with the etching-accelerator gas and the etching-suppressor gas used alternately, a high frequency is applied to substrate 28, and an inductive-coupling method with an external coil is used for the etching. The high frequency generates a negative bias potential in substrate 28 and makes positive ions in plasma, such as $SF_5^+$ or $CF_3^+$ collide with substrate 28, thus allows substrate 28 to be etched perpendicularly to the bottom.

The dry-etching may be suppressed by stopping the applying of the high frequency to substrate 28. The bias potential is stopped, and $CF^+$, material of a protective film, is not deflected. As a result, the protective film is formed uniformly on the walls of the through-holes in substrate 28.

The method described above is effectively applicable to forming an opening perpendicular to the bottom of the substrate by manufacturing methods described in Embodiments 1 and 2.

Figure 37:
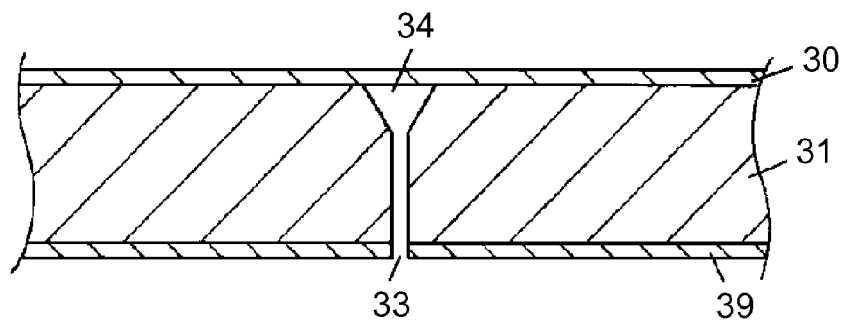
FIG. 37 is an enlarged sectional view of the device in accordance with Embodiment 3 for illustrating the method.

Next, as shown in FIG. 37, thin plate 31 is dry-etched until the hole reaches intermediate layer 30. In this process, a concentration of the etching-accelerator gas is gradually increased according to the progress of the etching toward the bottom of well 32. Alternatively, a time of the etching with the etching-accelerator gas is gradually increased. In other words, when facilitating of the dry-etching and suppressing of the dry-etching are alternately repeated, the ratio of a time of the facilitating to a time of the suppressing is gradually increased.

This operation allows the hole 33 to flaring toward well 32, as shown in FIG. 37, thus allowing through-hole 33 to communicate with pocket 34 flaring toward well 32. When the dry-etching is finished, i.e. when hole 33 reaches intermediate layer 30, the dry-etching is not necessarily stopped immediately due to intermediate layer 30 made from silicon dioxide since the etching gas does not etch intermediate layer 30 immediately.

The etching-accelerator gas of $SF_6$ cannot easily dry-etch intermediate layer 30 made of silicon dioxide to remove the intermediate layer since a ratio of an etching rate for silicon to that for silicon dioxide is more than ten. Therefore, even if the dry-etching continues for a while after the hole reaches the silicon dioxide layer, the dry-etching can hardly remove layer 30, thus forming pocket 34 accurately and easily.

Figure 38:
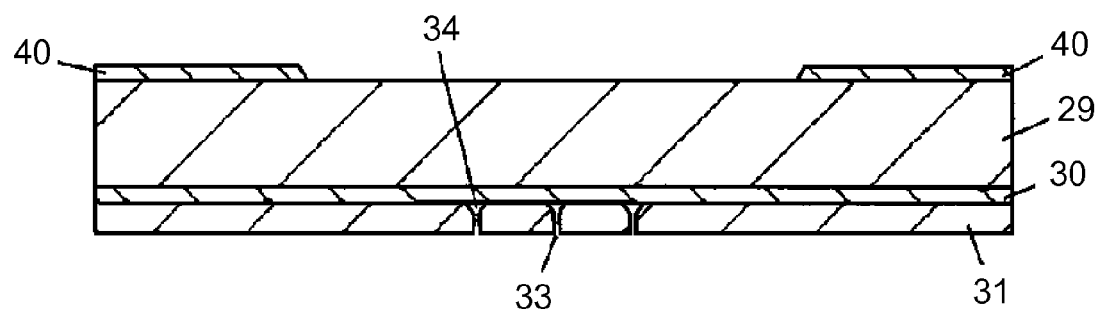
FIG. 38 is a sectional view of the device in accordance Embodiment 3 for illustrating the method.
Figure 39:
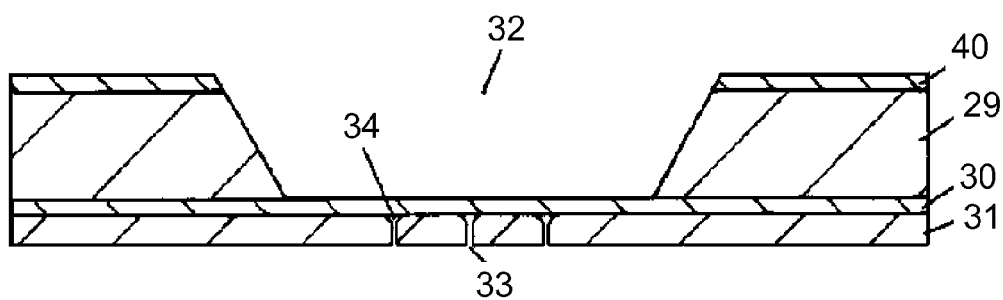
FIG. 39 is a sectional view of the device in accordance Embodiment 3 for illustrating the method.

Then, as shown in FIG. 38, resist mask 40 is provided on base 29 by a photo-lithography method. Then, as shown in FIG. 39, base 29 is etched until well 5 reaches intermediate layer 30. At this process, the etching-accelerator gas and the etching-suppressor gas may be used, as previously discussed, for providing wells 32 at a high density. However, if the high density is not needed, a wet-etching using TMAH or KOH is acceptable.

Figure 40:
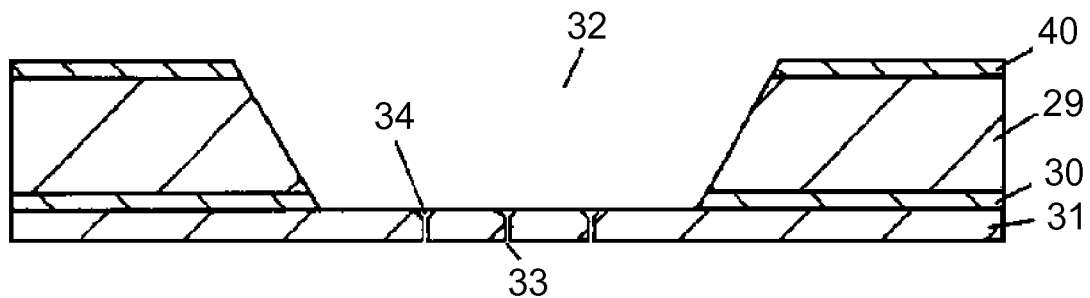
FIG. 40 is a sectional view of the device in accordance Embodiment 3 for illustrating the method.

Next, as shown in FIG. 40, a portion of intermediate layer 30 made of silicon dioxide exposed from the bottom of well 32 is removed by a wet-etching using HF or a dry-etching with $CF_4$ gas.

Figure 41:
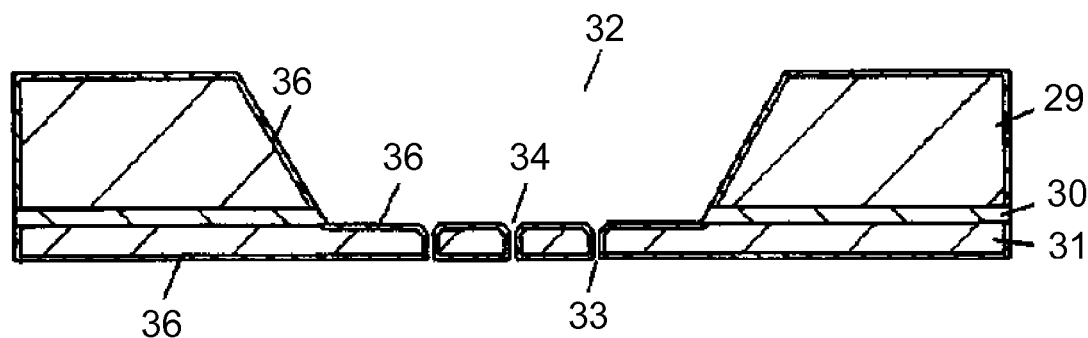
FIG. 41 is a sectional view of the device in accordance Embodiment 3 for illustrating the method.

Then, as shown in FIG. 41, a silicon-dioxide layer is formed on the surface of the silicon substrate, which includes base 29 and thin plate 31, by a thermal oxidation method. This process provides insulating layer 36 made from silicon dioxide on the inner wall and the bottom of well 32, the inner wall of pocket 34, the inner wall of hole 33, and the lower surface of thin plate 31.

Figure 42:
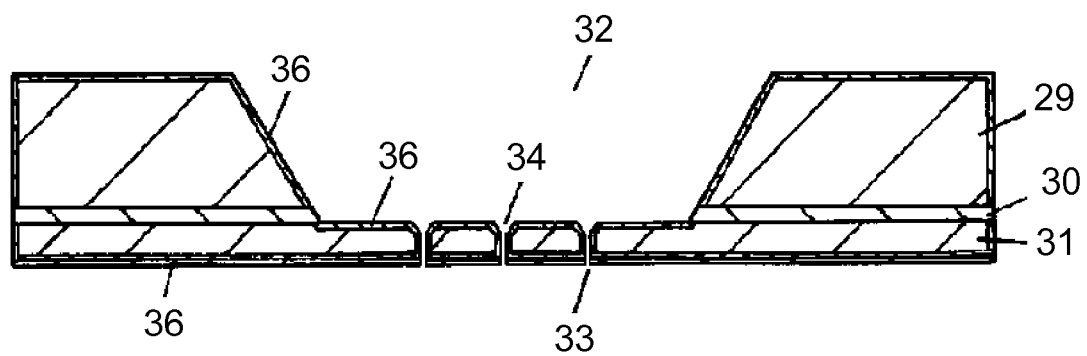
FIG. 42 is a sectional view of the device in accordance Embodiment 3 for illustrating the method.

Next, as shown in FIG. 42, detecting electrode 35 is formed on the lower surface of thin plate 31 by vapor-depositing or sputtering gold. Thus, electrode 35 is formed not only on the lower surface of plate 31 but also on the inner wall of through-hole 33. Electrode 35 is made of a material so as not to react on culture solution 38. The material may be preferably selected from gold, platinum, silver, silver chloride, and aluminum appropriately according to a type of the sample solution.

The method in accordance with Embodiment 3 described above provides the device having through-holes 33 in thin plate 31 and conical pockets 34 communicating with holes 33 to well 32 accurately and easily by a one-time etching.

In the method of Embodiment 3, it is not necessary that the substrate is etched with two kinds of resist masks by the photolithography method from the well. This method allows through-holes and pockets to be formed accurately in the bottom of the well even if the substrate has bumps and dips therein. Even the substrate having such rough surface may have the through-holes and the pockets in the bottom of the well accurately without using a spray-coating device which coat the rough surface uniformly with a resist mask, or using a projection or a stepper forming a highly accurate pattern onto the resist mask by exposure to light with non contact between a photo mask and the substrate.

Exemplary Embodiment 4

Figure 43:
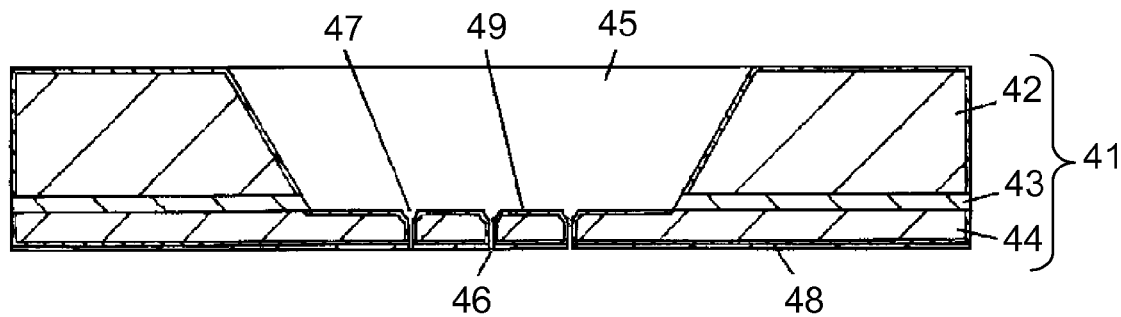
FIG. 43 is a sectional view of a device for measuring an extracellular potential in accordance with Exemplary Embodiment 4 of the invention.
Figure 44:
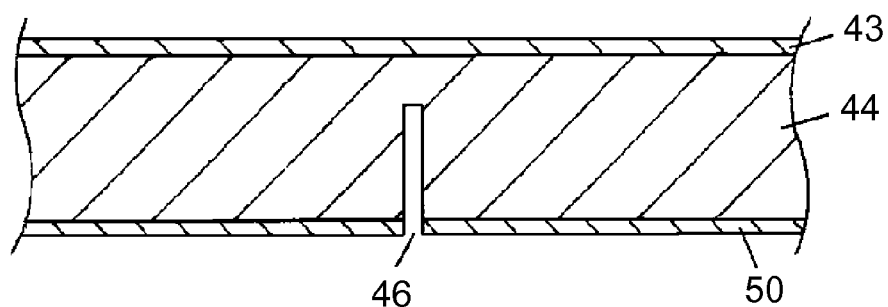
FIG. 44 is an enlarged sectional view the device in accordance with Embodiment 4 for illustrating a method of manufacturing the device.
Figure 45:
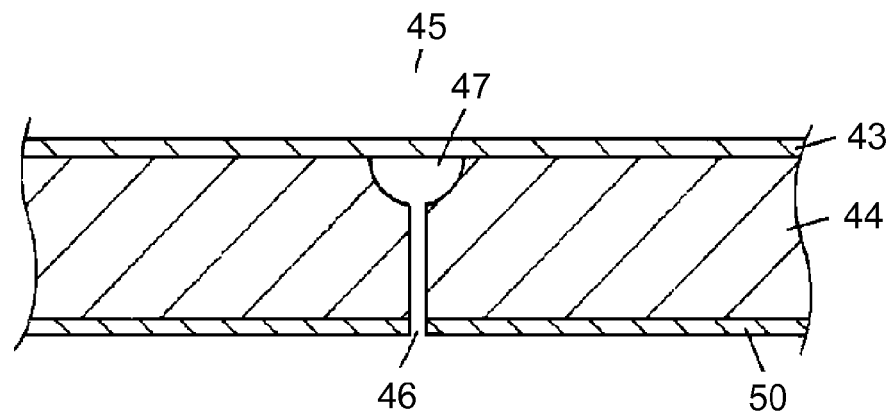
FIG. 45 is an enlarged sectional view of the device in accordance with Embodiment 4 for illustrating the method.

FIG. 43 is a sectional view of a device for measuring an extracellular potential in accordance with Exemplary Embodiment 5 of the present invention. FIGS. 44 and 45 are enlarged sectional views of essential portions of the device.

The device in accordance with Embodiment 5 has a structure basically identical to that of Embodiment 3, and thus, similar elements are not described.

FIG. 43 is a sectional view of the device in accordance with Embodiment 5. Pocket 47 formed in thin plate 44 has a hemisphere shape, which retains test cell 37 more closely thereto, so that a change of an electrical potential of culture solution 38 in through-hole 46 can be detected more easily.

A method of manufacturing the device will be described below. The method in accordance with Embodiment 4 is similar to that of Embodiment 3. According to Embodiment 4, through-hole 46 and pocket 47 is formed in thin plate 44 by a method different from that of Embodiment 3. The different method will be described with reference to FIGS. 44 and 45.

As shown in FIG. 44, resist mask 50 is formed on thin plate 44 while intermediate layer 43 and thin plate 44 are attached to each other. Then, thin plate 44 is dry-etched with etching-accelerator gas for facilitating the etching and etching-suppressor gas for suppressing the etching up to a predetermined depth to form through-hole 46. The predetermined depth is determined to prevent the etching from reaching intermediate layer 43 made of silicon dioxide, and determined to be an optimum depth in response to a size and a shape of pocket 47.

During this etching, thin plate 44 is etched with the etching-accelerator gas, and then has a protective film (not shown) formed thereon with the etching-suppressor gas. These processes for dry-etching thin plate 44 are repeated perpendicularly to resist mask 50 and only under an opening of resist mask 50. These processes terminate by dry-etching thin plate 44 with the etching-accelerator gas. This operation removes the protective film formed by the etching-suppressor gas from the bottom of the etched place.

Next, as shown in FIG. 45, pocket 47 is formed by dry-etching with $XeF_2$ gas. The dry-etching progresses from the bottom where silicon is exposed, and corroded area becomes greater as the etching progresses toward well 45. The inner wall of through-hole 46 has the protective film formed thereon by the etching-suppressor gas, so that the wall of hole 46 is not dry-etched by the $XeF_2$ gas. Pocket 47 thus has a hemisphere shape, as shown in FIG. 45 shows. After these processes discussed above, the substrate undergoes the processes shown in FIG. 38 through FIG. 42 similarly to that of Embodiment 3, thereby providing the device for measuring an extracellular potential.

Exemplary Embodiment 5

According to Exemplary Embodiment 5, another method for forming through-hole 33 and 46 and pocket 34 and 47 described in Embodiments 3 and 4, respectively, will be described.

The method of forming the through-hole different from the methods of Embodiments 3 and 4 will be described hereinafter with reference to FIG. 46 through FIG. 48.

Figure 46:
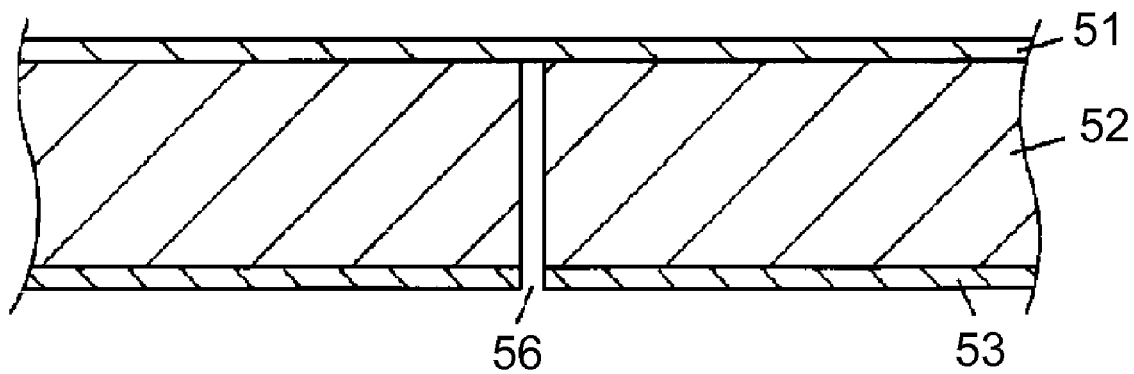
FIG. 46 is an enlarged sectional view of a device for measuring an extracellular potential in accordance with Exemplary Embodiment 5 of the invention for illustrating a method of manufacturing the device.
Figure 47:
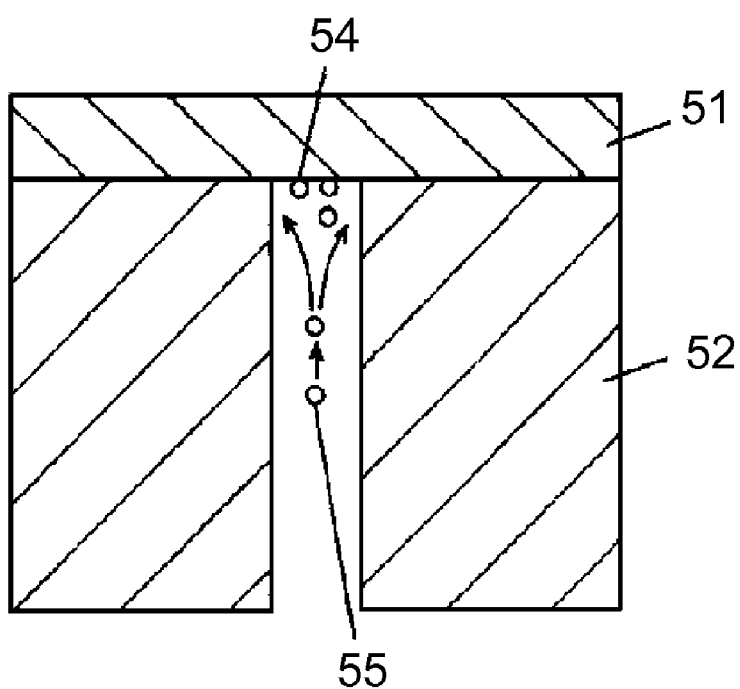
FIG. 47 is an enlarged sectional view of the device in accordance with Embodiment 5 for illustrating the method.

FIG. 46 is a sectional view of a measuring device in accordance with Embodiment 5 for illustrating a method of manufacturing the device. Intermediate layer 51 made of silicon dioxide and thin plate 52 made of silicon are stacked on each other. Then, resist mask 53 is provided on thin plate 52, and through-hole 56 is formed by dry-etching a substrate with etching-accelerator gas for facilitating the etching and etching-suppressor gas for suppressing the etching. Thin plate 52 is continued to etch until hole 56 reaches intermediate layer 51.

Thin plate is still continued to etch after hole 56 reaches intermediate layer 51 which is made of an insulator. Thin plate 52 made of silicon has a resistance smaller than intermediate layer 51. As shown in FIG. 47, excessive etching makes etching ions 54, such as $SF_5^+$, stay on the surface of layer 51 when the etching-accelerator gas is used for the dry-etching, so that etching ions 55 supplied from plasma deflects along an arrow shown in FIG. 47.

Figure 48:
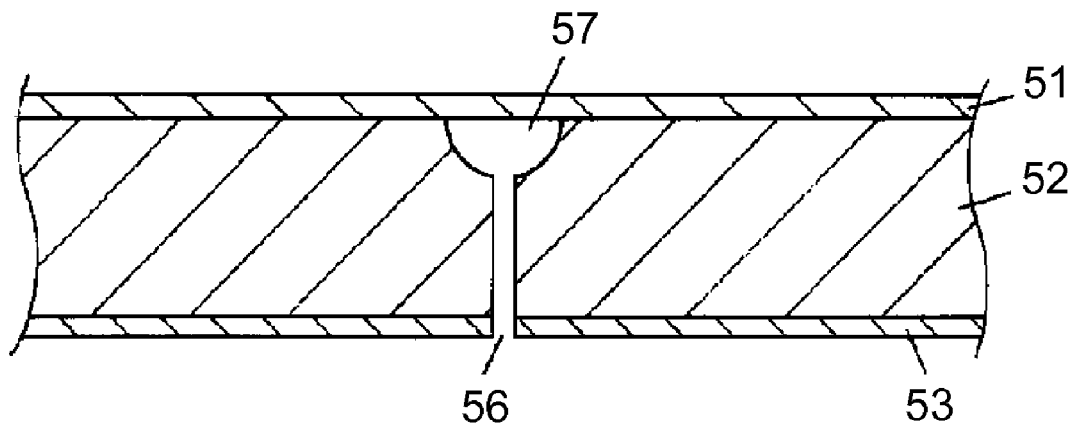
FIG. 48 is an enlarged sectional view of the device in accordance with Embodiment 5 for illustrating the method.

As a result, the vicinity of the wall of intermediate layer 51 is locally dry-etched, and through-hole 56 flares toward the well, namely, pocket 57 is formed, as shown in FIG. 48.

According to an experiment, thin plate 52 is continued to dry-etch after hole 56 having a diameter of 3 μm reaches intermediate layer 51, thereby providing pocket 57 having a maximum diameter of 10 μm.

INDUSTRIAL APPLICABILITY

A device for measuring an extracellular electric potential according to the present invention allows a test cell to enter in a hollow section of the device. Once the test cell enters in the hollow section, the cell is trapped therein securely. The device thus can detect an electric signal generated by activities of the cell without fail.

What is claimed is:

1. A device for measuring an extracellular potential of a test cell, said device comprising:
   a substrate including
      a base,
      an intermediate layer arranged on the base, and
      a plate arranged on the intermediate layer, wherein the plate has a first surface and a second surface opposite to the first surface, the first surface of the plate is situated on the intermediate layer, and wherein the plate includes a through-hole;
   a well formed in the base and the intermediate layer such that the well extends from the base to an exposed portion of the first surface of the plate, wherein the through-hole is arranged such that an opening of the through-hole opens to a bottom of the well so as to allow the well to communicate with the second surface of the plate, the through-hole having an inner wall surface which extends from the bottom of the well to the second surface of the plate;
   an insulator arranged such that a first portion of the insulator is provided on the exposed portion of the first surface of the plate within the well, the first portion of the insulator being connected to the intermediate layer, and such that a second portion of the insulator is provided on the base; and
   an electrode,
   wherein the intermediate layer has a resistivity greater than a resistivity of the plate,
   wherein the intermediate layer has a side surface exposed to an interior of the well, and the base has a side surface facing towards the interior of the well,
   wherein the second portion of the insulator is provided on the side surface of the base and is connected directly to the side surface of the intermediate layer so as to prevent the side surface of the base from being exposed to the interior of the well,
   wherein the electrode is arranged such that a first portion of the electrode is provided along the second surface of the plate, and such that a second portion of the electrode is provided along the inner wall surface of the through-hole, and
   wherein the through-hole is arranged to allow the test cell to be held at the opening of the through-hole.

2. The device of claim 1, wherein a diameter of the opening of the through-hole is smaller than a diameter of the test cell.

3. The device of claim 1, wherein the first portion of the insulator is provided on an entirety of the exposed portion of the first surface of the plate, but does not extend across the opening of the through-hole.

4. The device of claim 3, wherein the first portion of the insulator is further provided on all interior surface portions of the through-hole and on all interior surface portions of the opening of the through-hole.

5. The device of claim 1, wherein
   the first portion of the insulator is connected directly to the side surface of the intermediate layer.

6. The device of claim 5, wherein
   the base is made of a material different from that of the intermediate layer,
   the plate is made of a material different from that of the intermediate layer, and
   the first portion of the insulator is made of a material identical to that of the intermediate layer.

7. The device of claim 5, wherein
   the base comprises silicon,
   the intermediate layer and the first portion of the insulator are made of silicon dioxide, and
   the plate comprises silicon.

8. The device of claim 1, wherein
   the base is made of a material different from that of the intermediate layer,
   the plate is made of a material different from that of the intermediate layer, and
   the first portion of the insulator is made of a material identical to that of the intermediate layer.

9. The device of claim 8, wherein the second portion of the insulator is made of a material identical to that of the intermediate layer.

10. The device of claim 9, wherein
    the base comprises silicon,
    the intermediate layer, the first portion of the insulator, and the second portion of the insulator are made of silicon dioxide, and
    the plate comprises silicon.

11. The device of claim 1, wherein the intermediate layer and the plate are arranged so as to be in direct contact with each other.

* * * * *